(12) United States Patent
Cirillo et al.

(10) Patent No.: US 8,957,063 B2
(45) Date of Patent: *Feb. 17, 2015

(54) AMINE AND ETHER COMPOUNDS WHICH MODULATE THE CB2 RECEPTOR

(75) Inventors: Pier Francesco Cirillo, Woodbury, CT (US); Eugene Richard Hickey, Danbury, CT (US); Doris Riether, Newtown, CT (US); Monika Ermann, Wantage (GB); Innocent Mushi, Didcot (GB)

(73) Assignee: Boehringer Ingelheim International GmbH, Ingelheim am Rhein ( * ) Notice: Subject to any disclaimer, the term of this patent is extended or adjusted under 35 U.S.C. 154(b) by 410 days.

This patent is subject to a terminal disclaimer.

(21) Appl. No.: 12/867,970

(22) PCT Filed: Feb. 19, 2009

(86) PCT No.: PCT/US2009/034464
§ 371 (c)(1),
(2), (4) Date: Sep. 14, 2010

(87) PCT Pub. No.: WO2009/105509
PCT Pub. Date: Aug. 27, 2009

(65) Prior Publication Data
US 2011/0190256 A1 Aug. 4, 2011

Related U.S. Application Data

(60) Provisional application No. 61/030,386, filed on Feb. 21, 2008.

(51) Int. Cl.
| | | |
|---|---|---|
| A61K 31/397 | (2006.01) | |
| A61K 31/54 | (2006.01) | |
| A61K 31/5377 | (2006.01) | |
| A61K 31/4523 | (2006.01) | |
| A61K 31/4427 | (2006.01) | |
| A61K 31/44 | (2006.01) | |
| A61K 31/42 | (2006.01) | |
| A61K 31/4196 | (2006.01) | |
| C07D 279/12 | (2006.01) | |
| C07D 413/00 | (2006.01) | |
| C07D 413/02 | (2006.01) | |
| C07D 211/68 | (2006.01) | |
| C07D 401/02 | (2006.01) | |
| C07D 405/02 | (2006.01) | |
| C07D 213/02 | (2006.01) | |
| C07D 261/06 | (2006.01) | |
| C07D 261/16 | (2006.01) | |
| C07D 213/75 | (2006.01) | |
| C07D 405/12 | (2006.01) | |
| C07D 413/12 | (2006.01) | |

(52) U.S. Cl.
CPC ............ *C07D 261/16* (2013.01); *C07D 213/75* (2013.01); *C07D 405/12* (2013.01); *C07D 413/12* (2013.01)

USPC .................. 514/210.2; 514/227.8; 514/236.8; 514/318; 514/326; 514/352; 514/380; 514/383; 544/58.2; 544/58.7; 544/137; 546/193; 546/209; 546/272.1; 546/309; 548/246; 548/265.4

(58) Field of Classification Search
USPC ........ 514/210.2, 227.8, 236.8, 318, 326, 352, 514/380, 383; 544/58.2, 58.7, 137; 546/193, 209, 272.1, 309; 548/246, 548/265.4

See application file for complete search history.

(56) References Cited

U.S. PATENT DOCUMENTS

| | | |
|---|---|---|
| 3,116,284 A | 12/1963 | Testa |
| 3,117,128 A | 1/1964 | Mooradian |
| 5,834,401 A | 11/1998 | Kawamura et al. |
| 7,476,756 B2 | 1/2009 | Almario-Garcia et al. |
| 7,595,397 B2 | 9/2009 | Zindell et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 8,329,735 B2 | 12/2012 | Ermann et al. |
| 2004/0209865 A1 | 10/2004 | Stenkamp et al. |
| 2004/0242666 A1 | 12/2004 | Chen |
| 2005/0107381 A1 | 5/2005 | Chen |
| 2006/0009457 A1 | 1/2006 | Hoffmann et al. |
| 2008/0039464 A1 | 2/2008 | Berry et al. |
| 2008/0081822 A1 | 4/2008 | Berry et al. |
| 2009/0275611 A1 | 11/2009 | Riether et al. |

(Continued)

FOREIGN PATENT DOCUMENTS

| | | |
|---|---|---|
| DE | 1080563 B | 12/1957 |
| GB | 839943 A | 6/1960 |

(Continued)

OTHER PUBLICATIONS

Takada, Toshikazu. Pharmacological studies of a new local anesthetic, 2'-methyl-2-methyl-2-n-propylaminopropionanilide hydrochloride (LA-012). Nippon Yakurigaku Zasshi. (1966), 62(3), 64-74.*

(Continued)

*Primary Examiner* — Samantha Shterengarts
(74) *Attorney, Agent, or Firm* — Michael P. Morris; Anthony P. Bottino

(57) ABSTRACT

Compounds which modulate the CB2 receptor are disclosed. The compounds are useful for treating CB2 receptor-mediated diseases such as pain.

5 Claims, No Drawings

(56) References Cited

U.S. PATENT DOCUMENTS

| | | |
|---|---|---|
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |

FOREIGN PATENT DOCUMENTS

| | | | |
|---|---|---|---|
| GB | 853799 A | 11/1960 | |
| GB | 884258 A | 12/1961 | |
| GB | 1170856 * | 11/1969 | 564/305 |
| GB | 1237126 A | 6/1971 | |
| JP | 61126071 A | 6/1986 | |
| JP | 8151364 A | 6/1996 | |
| JP | 8311026 A | 11/1996 | |
| JP | 2006511492 A | 4/2006 | |
| JP | 2006525990 A | 11/2006 | |
| JP | 2007501242 A | 1/2007 | |
| WO | 02094825 A1 | 11/2002 | |
| WO | 2004026301 A1 | 4/2004 | |
| WO | 2004099200 A1 | 11/2004 | |
| WO | 2006074445 A2 | 7/2006 | |
| WO | 2006080040 A1 | 8/2006 | |
| WO | 2006117461 A2 | 11/2006 | |
| WO | 2007070760 A2 | 6/2007 | |
| WO | 2007104034 A2 | 9/2007 | |
| WO | 2007118041 A1 | 10/2007 | |
| WO | 2007140385 A2 | 12/2007 | |
| WO | 2008014199 A2 | 1/2008 | |
| WO | 2008039645 A1 | 4/2008 | |
| WO | 2008048914 A1 | 4/2008 | |
| WO | 2008064054 A2 | 5/2008 | |
| WO | 2008098025 A1 | 8/2008 | |
| WO | 2009055357 A1 | 4/2009 | |
| WO | 2009061652 A1 | 5/2009 | |
| WO | 2009105509 A1 | 8/2009 | |
| WO | 2009140089 A2 | 11/2009 | |
| WO | 2010005782 A1 | 1/2010 | |
| WO | 2010036630 A2 | 4/2010 | |
| WO | 2010036631 A2 | 4/2010 | |
| WO | 2010077836 A2 | 7/2010 | |
| WO | 2010096371 A2 | 8/2010 | |
| WO | 2010147791 A1 | 12/2010 | |
| WO | 2010147792 A2 | 12/2010 | |
| WO | 2011037795 | 3/2011 | |
| WO | 2011088015 A1 | 7/2011 | |
| WO | 2011109324 A1 | 9/2011 | |
| WO | 2012012307 A1 | 1/2012 | |

OTHER PUBLICATIONS

Ito, Nobuyuki. Cancer Science 94(1), (2003) 3-8.*
Database Registry Chemical Abstracts Service, Columbus, Ohio, Accession No. RN 873553-80-1, Entered STN: Feb. 6, 2006.*
ChemAbstracts, Ukraine. Order Nos. T6110295, T5962700, T5962703 abstract and "Enamine Screening Library", Jan. 1, 2009, Enamine, 23 Alexandra Matrosova St., 01103 Kiev, Ukraine.
International Search Report for PCT/US2009/034464 mailed Jun. 3, 2009.
Shojiro, U. et al., "Synthesis of 5-(Aminoacylamido)-3-methylisoxazole Derivatives and Their Analgesic Action." Faculty of Pharmacy, Kyoto University and Institute for Chemical Research, 1962, vol. 83, pp. 198-200.

* cited by examiner

AMINE AND ETHER COMPOUNDS WHICH MODULATE THE CB2 RECEPTOR

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, includung B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various imflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J. Pharmacol. (2005) 520:164-171 and Smith et al., The anti-inflammatory activities of cannabinoid receptor ligands in mouse peritonitis models Eur J. Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J. Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

BRIEF SUMMARY OF THE INVENTION

The present invention provides novel compounds which bind to and modulate the CB2 receptor. The invention also provides a method and pharmaceutical compositions for treating inflammation by way of the administration of therapeutic amounts of these compounds. Lastly, the invention provides a method and pharmaceutical compositions for treating pain by way of the administration of therapeutic amounts of the new compounds which are CB2 agonists.

DETAILED DESCRIPTION OF THE INVENTION

In its broadest generic aspect the invention provides compounds of formula I, wherein

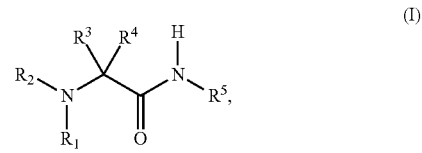

(I)

$R^1$ is hydrogen, $C_{1-10}$ alkyl or $C_{3-10}$ cycloalkyl, each optionally halogenated or substituted with 1-3 $C_{1-10}$ alkyl optionally halogenated;

$R^2$ is $C_{1-10}$ alkyl, $C_{3-10}$ cycloalkyl, arylsulfonyl, arylcarbonyl, $C_{1-10}$ acyl, $C_{3-10}$ cycloalkylcarbonyl, heterocyclylcarbonyl, heteroarylcarbonyl, heterocyclyl, benzyl, phenethyl, aryl or heteroaryl each optionally independently substituted with 1 to 3 substituents chosen from $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, $C_{1-6}$ alkylamino, $C_{3-6}$ cycloalkylamino, $C_{1-6}$ dialkylamino, $C_{1-6}$ alkylaminocarbonyl, $C_{1-6}$ acylamino, $C_{1-6}$ dialkylaminocarbonyl, hydroxyl, halogen, cyano, nitro, oxo, heterocyclyl, aryl and heteroaryl, each substituent on $R^2$ where possible is optionally halogenated or substituted with 1 to 3 $C_{1-6}$ alkyl, $C_{1-6}$ acyl, $C_{1-6}$ alkyl sulfonyl, cyano, aryl, oxo or hydroxyl;

or $R^1$ and $R^2$ together with the nitrogen atom to which they are attached form a monocyclic, bicyclic or spirocyclic heterocycle or monocyclic or bicyclic heteroaryl ring each optionally substituted with 1 to 3 $C_{1-6}$ alkyl, $C_{1-6}$ alkoxy, $C_{1-6}$ acyl, $C_{1-6}$ alkyl sulfonyl, cyano, aryl, oxo, hydroxyl or halogen each ring substituent being further optionally halogenated where possible;

$R^3$ and $R^4$ are independently hydrogen or $C_{1-6}$ alkyl optionally halogenated with the proviso that $R^3$ and $R^4$ cannot simultaneously be hydrogen; or $R^3$ and $R^4$ together with the carbon atom to which they are attached form a 3- to 6-membered cycloalkyl or heterocyclic ring each optionally halogenated;

$R^5$ is aryl or 5- to 6-membered heteroaryl each substituted with 1 to 3 substituents chosen from $C_{1-6}$ alkyl, heterocyclyl, $C_{1-6}$ alkoxy, $C_{3-6}$ cycloalkyl, aryloxy, halogen, cyano, dimethylamino $C_{1-4}$alkyl, aryl, thienyl and pyridinyl;

each substituent on $R^5$ is optionally halogenated or substituted with 1 to 3 $C_{1-4}$ alkyl optionally halogenated;

or a pharmaceutically acceptable salt thereof.

In a first subgeneric aspect, the invention provides compounds of the formula I wherein, $R^1$ is hydrogen, $C_{1-6}$ alkyl or $C_{3-7}$ cycloalkyl, each optionally halogenated or substituted with 1-3 $C_{1-6}$ alkyl optionally halogenated;

$R^2$ is thiomorpholinylcarbonyl, 1,1-dioxo-1$\lambda^6$-thiomorpholinylcarbonyl, morpholinylcarbonyl, phenylsulfonyl, phenylcarbonyl, phenyl, pyridinyl, pyrimidinyl or thiazolyl, each optionally independently substituted with 1 to 3 substituents chosen from $C_{1-5}$ alkyl, $C_{1-5}$ cycloalkyl, $C_{1-5}$ alkoxy, $C_{1-5}$ alkylthio, $C_{1-5}$ alkylsulfonyl, $C_{1-5}$ alkoxycarbonyl, $C_{1-5}$ alkylamino, $C_{3-6}$ cycloalkylamino, $C_{1-5}$ dialkylamino, $C_{1-5}$ alkylaminocarbonyl, $C_{1-5}$ acylamino, $C_{1-5}$ dialkylaminocarbonyl, hydroxyl, halogen, cyano, nitro, each $R^2$ substituent where possible is optionally halogenated or substituted with 1 to 3 $C_{1-5}$ alkyl, $R^3$ and $R^4$ each methyl optionally halogenated, or $R^3$ and $R^4$ together with the carbon atom to which they are attached form a cyclopropyl or cyclobutyl ring each optionally halogenated;

$R^5$ is phenyl, naphthyl, pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$ alkyl, phenyl, thienyl and pyridinyl, each substituent on $R^5$ is optionally halogenated or substituted with 1 to 3 $C_{1-4}$ alkyl optionally halogenated.

In another subgeneric aspect, the invention provides compounds of the formula I wherein, $R^1$ is hydrogen, $C_{1-6}$ alkyl or $C_{3-7}$ cycloalkyl, each optionally halogenated or substituted with 1-3 $C_{1-6}$ alkyl optionally halogenated;

$R^2$ is $C_{1-6}$ alkyl, $C_{3-7}$ cycloalkyl, 1,1-dioxo-1$\lambda^6$-thiomorpholinylcarbonyl, phenylsulfonyl, tetrahydropyranyl, tetrahydrofuranyl, pyrrolidinyl or piperidinyl, each optionally independently substituted with 1 to 3 substituents chosen from $C_{1-5}$ alkyl, $C_{1-5}$ cycloalkyl, $C_{1-5}$ alkoxy, $C_{1-5}$ alkylthio, $C_{1-5}$ alkylsulfonyl, $C_{1-5}$ alkoxycarbonyl, $C_{1-5}$ alkylamino, $C_{3-6}$ cycloalkylamino, $C_{1-5}$ dialkylamino, $C_{1-5}$ alkylaminocarbonyl, $C_{1-5}$ acylamino, $C_{1-5}$ dialkylaminocarbonyl, hydroxyl, halogen, cyano, nitro, oxo, phenyl and heterocyclyl chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl and piperazinyl, each $R^2$ substituent where possible is optionally halogenated or substituted with 1 to 3 $C_{1-5}$ alkyl, $C_{1-5}$ acyl, methyl sulfone, cyano, phenyl, oxo or hydroxyl;

or $R^1$ and $R^2$ together with the nitrogen atom to which they are attached form a ring chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl, piperazinyl, azetidinyl, benzimidazolyl, pyrazolyl, imidazolyl, triazinyl, indazolyl, indolyl, indolinyl, isoindolyl, isoindolinyl, and 2-aza-spiro[4.5]dec-2-yl, 1-aza-spiro[4.5]dec-1-yl, 1-aza-spiro[4.4]non-1-yl, 2-aza-spiro[4.4]non-2-yl, 2-aza-spiro[5.5]undec-2-yl, 1-aza-spiro[5.5]undec-1-yl each optionally substituted with 1 to 3 $C_{1-6}$ alkyl, $C_{1-6}$ alkoxy, $C_{1-6}$ acyl, $C_{1-6}$ alkyl sulfonyl, cyano, phenyl, oxo, hydroxyl and halogen each ring substituent being further optionally halogenated where possible;

$R^3$ and $R^4$ are each methyl or ethyl, each optionally halogenated, or $R^3$ and $R^4$ together with the carbon atom to which they are attached form a cyclopropyl or cyclobutyl ring each optionally halogenated;

$R^5$ is phenyl, naphthyl, pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$ alkyl, phenyl, thienyl and pyridinyl, each substituent on $R^5$ is optionally halogenated or substituted with 1 to 3 $C_{1-4}$ alkyl optionally halogenated.

In a further subgeneric aspect, the invention provides compounds of the formula I wherein, $R^1$ is hydrogen or $C_{1-3}$ alkyl optionally halogenated;

$R^2$ is $C_{1-6}$ alkyl or $C_{3-7}$ cycloalkyl optionally independently substituted with 1 to 3 halogen, one $C_{3-7}$ cycloalkyl or one heterocyclyl chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl, piperazinyl, optionally halogenated or substituted with $C_{1-4}$ alkyl;

or $R^1$ and $R^2$ together with the nitrogen atom to which they are attached form a ring chosen from thiomorpholinyl, 1,1-dioxo-1$\lambda^6$-thiomorpholinyl, morpholinyl, pyrrolidinyl, piperidinyl, azetidinyl, indolyl, indolinyl, isoindolyl, isoindolinyl, and 2-aza-spiro[4.5]dec-2-yl each optionally substituted with 1 to 3 $C_{1-4}$ alkyl, $C_{1-4}$ alkoxy and halogen each ring substituent being further optionally halogenated where possible;

$R^3$ and $R^4$ are each methyl or ethyl or $R^3$ and $R^4$ together with the carbon atom to which they are attached form a cyclopropyl or cyclobutyl ring;

$R^5$ is pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$alkyl, phenyl thienyl and pyridinyl, each substituent on $R^5$ is optionally halogenated or substituted with 1 to 3 $C_{1-4}$ alkyl optionally halogenated.

In a further subgeneric aspect, the invention provides compounds of the formula I wherein, $R^3$ and $R^4$ are each methyl;

$R^5$ is pyridinyl, pyrazolyl, triazolyl, isoxazolyl, thiadiazolyl, oxadiazoyl or thiazolyl each substituted with 1 to 2 substituents chosen from, methyl, ethyl, iso-propyl, tert-butyl, iso-butyl, neopentyl, cyclopropyl, cyclobutyl, cyclopentyl, cyclohexyl, trifluoromethyl or phenyl which is optionally substituted with a chlorine atom.

In a further subgeneric aspect, the invention provides compounds of the formula I wherein, $R^2$ is methyl optionally substituted with one heterocyclyl chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl, piperazinyl, optionally halogenated or substituted with $C_{1-4}$ alkyl or methyl sulfonyl;

or $R^1$ and $R^2$ together with the nitrogen atom to which they are attached form a ring chosen from thiomorpholinyl, 1,1-dioxo-1$\lambda^6$-thiomorpholinyl, morpholinyl, pyrrolidinyl, piperidinyl, azetidinyl, indolyl and 2-aza-spiro[4.5]dec-2-yl each optionally substituted with 1 to 3 $C_{1-3}$ alkyl, $C_{1-3}$ alkoxy and halogen each ring substituent being further optionally halogenated where possible;

$R^5$ is pyridinyl, triazolyl or isoxazolyl, each substituted with 1 to 2 substituents chosen from methyl, ethyl, tert-butyl, neopentyl, cyclohexyl, trifluoromethyl and phenyl which is optionally substituted with a chlorine atom.

In a further subgeneric aspect, the invention provides compounds of the formula I wherein, $R^1$ and $R^2$ together with the nitrogen atom to which they are attached form a ring chosen from thiomorpholinyl, 1,1-dioxo-1$\lambda^6$-thiomorpholinyl, morpholinyl, pyrrolidinyl, piperidinyl, azetidinyl, indolyl and 2-aza-spiro[4.5]dec-2-yl each optionally substituted with 1 to 3 $C_{1-3}$ alkyl, $C_{1-3}$ alkoxy and halogen each ring substituent being further optionally halogenated where possible.

In its second broadest generic aspect the invention provides compounds of formula II, wherein,

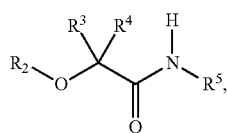

(II)

$R^2$ is $C_{1-10}$alkyl, $C_{3-10}$ cycloalkyl, heterocyclyl, benzyl, phenethyl, aryl or heteroaryl each optionally independently substituted with 1 to 3 substituents chosen from $C_{1-6}$ alkyl, $C_{3-10}$ cycloalkyl, $C_{1-6}$ alkoxy, $C_{1-6}$ alkylthio, $C_{1-6}$ alkylsulfonyl, $C_{1-6}$ alkoxycarbonyl, $C_{1-6}$ alkylamino, $C_{3-6}$ cycloalkylamino, $C_{1-6}$ dialkylamino, $C_{1-6}$ alkylaminocarbonyl, $C_{1-6}$ acylamino, $C_{1-6}$ dialkylaminocarbonyl, hydroxyl, halogen, cyano, nitro, oxo, heterocyclyl, aryl and heteroaryl, each substituent on $R^2$ where possible is optionally halogenated or substituted with 1 to 3 $C_{1-6}$ alkyl, $C_{1-6}$ acyl, $C_{1-6}$ alkyl sulfonyl, cyano, aryl, oxo or hydroxyl;

$R^3$ and $R^4$ are independently hydrogen or $C_{1-6}$ alkyl optionally halogenated with the proviso that $R^3$ and $R^4$ cannot simultaneously be hydrogen; or $R^3$ and $R^4$ together with the carbon atom to which they are attached form a 3- to 6-membered cycloalkyl or heterocyclic ring each optionally halogenated;

$R^5$ is aryl or 5- to 6-membered heteroaryl each substituted with 1 to 3 substituents chosen from $C_{1-6}$ alkyl, heterocyclyl, $C_{1-6}$ alkoxy, $C_{3-6}$ cycloalkyl, aryloxy, halogen, cyano, dimethylamino$C_{1-4}$alkyl, aryl, thienyl and pyridinyl, each substituent on $R^5$ is optionally halogenated or substituted with 1 to 3 $C_{1-4}$ alkyl optionally halogenated;

or a pharmaceutically acceptable salt thereof.

In a first subgeneric aspect, the invention provides compounds of the formula II wherein, $R^2$ is phenyl, pyridyl, pyrimidyl or thiazoyl, each optionally independently substituted with 1 to 3 substituents chosen from $C_{1-5}$ alkyl, $C_{1-5}$ cycloalkyl, $C_{1-5}$ alkoxy, $C_{1-5}$ alkylthio, $C_{1-5}$ alkylsulfonyl, $C_{1-5}$ alkoxycarbonyl, $C_{1-5}$ alkylamino, $C_{3-6}$ cycloalkylamino, $C_{1-5}$dialkylamino, $C_{1-5}$ alkylaminocarbonyl, $C_{1-5}$ acylamino, $C_{1-5}$ dialkylaminocarbonyl, hydroxyl, halogen, cyano, nitro;

each $R^2$ substituent where possible is optionally halogenated or substituted with 1 to 3 $C_{1-5}$alkyl, $C_{1-5}$ acyl, $C_{1-6}$ alkyl sulfonyl, cyano, phenyl, oxo or hydroxyl;

$R^3$ and $R^4$ each methyl or ethyl, each optionally halogenated, or $R^3$ and $R^4$ together with the carbon atom to which they are attached form a cyclopropyl or cyclobutyl ring each optionally halogenated;

$R^5$ is phenyl, naphthyl, pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$ alkyl, phenyl, thienyl and pyridinyl, each substituent on $R^5$ is optionally halogenated or substituted with 1 to 3 $C_{1-4}$ alkyl optionally halogenated.

In a another subgeneric aspect, the invention provides compounds of the formula II wherein, $R^2$ is $C_{1-6}$ alkyl, $C_{3-7}$ cycloalkyl, tetrahydropyranyl, tetrahydrofuranyl, pyrrolidinyl or piperidinyl, each optionally independently substituted with 1 to 3 substituents chosen from $C_{1-5}$alkyl, $C_{1-5}$ cycloalkyl, $C_{1-5}$ alkoxy, $C_{1-5}$ alkylthio, $C_{1-5}$ alkylsulfonyl, $C_{1-5}$ alkoxycarbonyl, $C_{1-5}$ alkylamino, $C_{3-6}$ cycloalkylamino, $C_{1-5}$ dialkylamino, $C_{1-5}$ alkylaminocarbonyl, $C_{1-5}$ acylamino, $C_{1-5}$ dialkylaminocarbonyl, hydroxyl, halogen, cyano, nitro, oxo, phenyl and heterocyclyl chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl and piperazinyl, each $R^2$ substituent where possible is optionally halogenated or substituted with 1 to 3 $C_{1-5}$alkyl, $C_{1-5}$ acyl, $C_{1-6}$ alkyl sulfonyl, cyano, phenyl, oxo or hydroxyl;

$R^3$ and $R^4$ each methyl or ethyl, each optionally halogenated, or $R^3$ and $R^4$ together with the carbon atom to which they are attached form a cyclopropyl or cyclobutyl ring each optionally halogenated;

$R^5$ is phenyl, naphthyl, pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$ alkyl, phenyl, thienyl and pyridinyl, each substituent on $R^5$ is optionally halogenated or substituted with 1 to 3 $C_{1-4}$ alkyl optionally halogenated.

In a further subgeneric aspect, the invention provides compounds of the formula II wherein, $R^2$ is $C_{1-6}$ alkyl or $C_{3-7}$ cycloalkyl optionally independently substituted with 1 to 3 halogen, $C_{3-7}$ cycloalkyl or one heterocyclyl chosen from tetrahydropyranyl, dioxanyl, tetrahydrofuranyl, thiomorpholinyl, 1,1-dioxo-1$\lambda^6$-thiomorpholinyl, morpholinyl, pyrrolidinyl, piperidinyl, piperazinyl, optionally halogenated or substituted with $C_{1-4}$ alkyl;

$R^3$ and $R^4$ each methyl or ethyl, or $R^3$ and $R^4$ together with the carbon atom to which they are attached form a cyclopropyl or cyclobutyl ring;

$R^5$ is pyridinyl, pyrrolyl, pyrazolyl, imidazolyl, oxazolyl, isoxazolyl, thiazolyl, isothiazolyl, triazolyl, oxadiazolyl or thiadiazolyl, each substituted with 1 to 3 substituents chosen from $C_{1-6}$ alkyl, $C_{1-6}$ alkoxy, $C_{3-6}$ cycloalkyl, phenoxy, halogen, cyano, dimethylamino$C_{1-4}$alkyl, phenyl thienyl and pyridinyl, each substituent on $R^5$ is optionally halogenated or substituted with 1 to 3 $C_{1-4}$ alkyl optionally halogenated.

In a further subgeneric aspect, the invention provides compounds of the formula II wherein,
$R^2$ is methyl optionally substituted with one heterocyclyl chosen from tetrahydropyranyl, dioxanyl, tetrahydrofuranyl, thiomorpholinyl, 1,1-dioxo-$1\lambda^6$-thiomorpholinyl, morpholinyl, pyrrolidinyl, piperidinyl, piperazinyl, indazolyl optionally halogenated or substituted with $C_{1-4}$alkyl;
$R^3$ and $R^4$ are each methyl;
$R^5$ is pyridinyl, pyrazolyl, triazolyl, isoxazolyl, thiadiazolyl, oxadiazoyl or thiazolyl each substituted with 1 to 2 substituents chosen from, methyl, ethyl, iso-propyl, tert-butyl, iso-butyl, neopentyl, cyclopropyl, cyclobutyl, cyclopentyl, cyclohexyl, trifluoromethyl or phenyl which is optionally substituted with a chlorine atom.

In a further subgeneric aspect, the invention provides compounds of the formula II wherein,
$R^5$ is pyridinyl, triazolyl or isoxazolyl, each substituted with 1 to 2 substituents chosen from methyl, ethyl, tert-butyl, neopentyl, cyclohexyl, trifluoromethyl and phenyl which is optionally substituted with a chlorine atom.

In another subgeneric aspect, the invention provides compounds of the formula III:

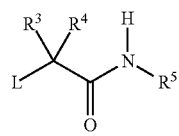

wherein for the formula (III)

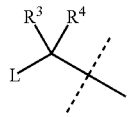

is chosen independently from members of column A in Table I, and

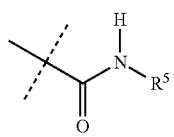

is chosen independently from members of column B in Table I:

TABLE I (and TABLE I-continued) — columns A and B contain chemical structures.

TABLE I-continued
| A | B |
|---|---|
| 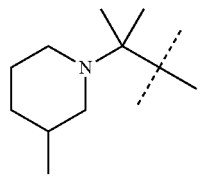 | |
| 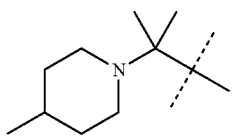 | |
| 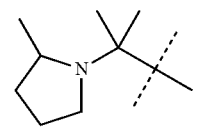 | |
| 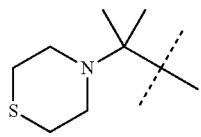 | |
| 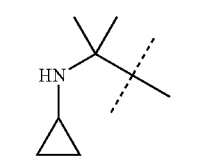 | |
| 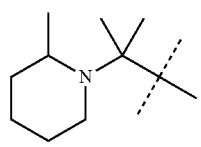 | |
| 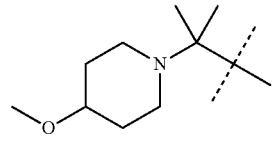 | |
| 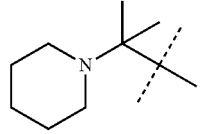 | |
| 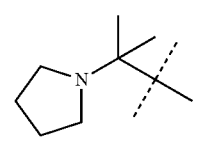 | |
| 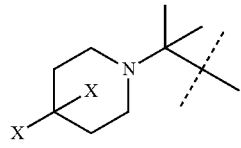 | |
| 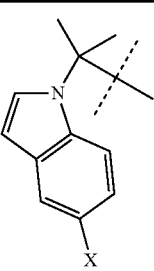 | |
| 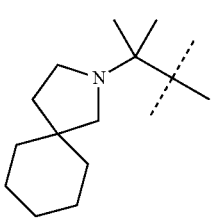 | |
| 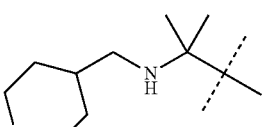 | |
| 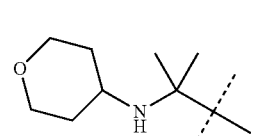 | |
| 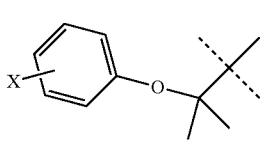 | |
| 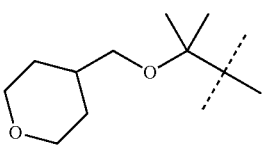 | |
| 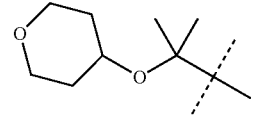 | |
| 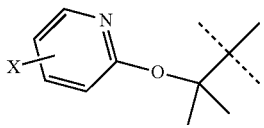 | |
| 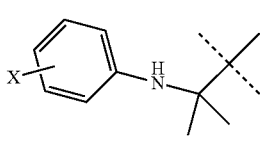 | |

TABLE I-continued

| A | B |
|---|---|
| 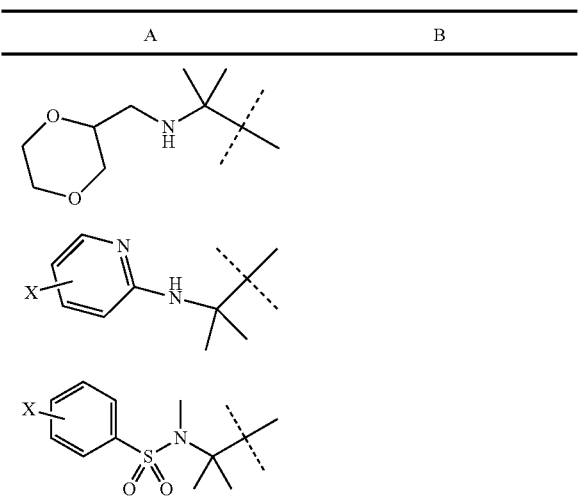 | |

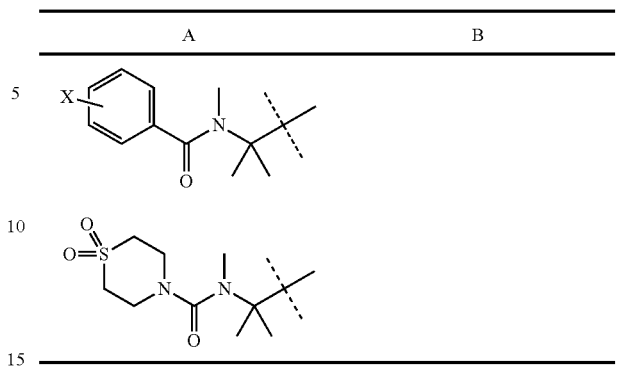

wherein X in each case is halogen or $CH_3$ optionally halogenated;
or a pharmaceutically acceptable salt thereof.

In another embodiment, the invention provides compounds in Table II which can be made in view of the general schemes, examples and methods known in the art.

TABLE II

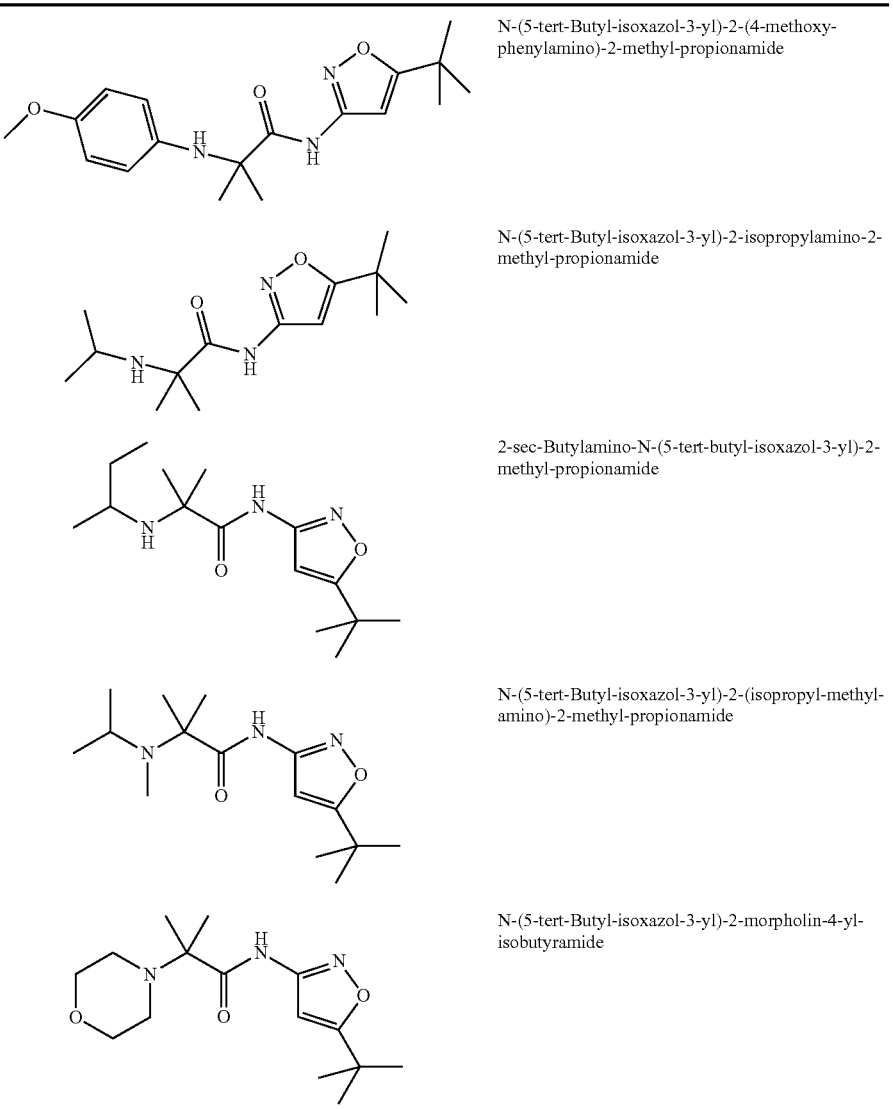

N-(5-tert-Butyl-isoxazol-3-yl)-2-(4-methoxy-phenylamino)-2-methyl-propionamide

N-(5-tert-Butyl-isoxazol-3-yl)-2-isopropylamino-2-methyl-propionamide 2-sec-Butylamino-N-(5-tert-butyl-isoxazol-3-yl)-2-methyl-propionamide N-(5-tert-Butyl-isoxazol-3-yl)-2-(isopropyl-methyl-amino)-2-methyl-propionamide N-(5-tert-Butyl-isoxazol-3-yl)-2-morpholin-4-yl-isobutyramide TABLE II-continued

| | |
|---|---|
| 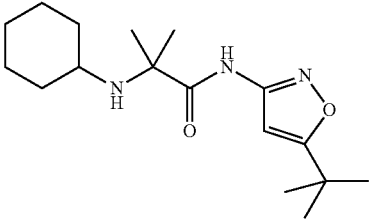 | N-(5-tert-Butyl-isoxazol-3-yl)-2-cyclohexylamino-2-methyl-propionamide |
| 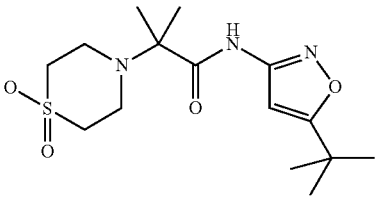 | N-(5-tert-Butyl-isoxazol-3-yl)-2-(1,1-dioxo-1$\lambda^6$-thiomorpholin-4-yl)-isobutyramide |
| 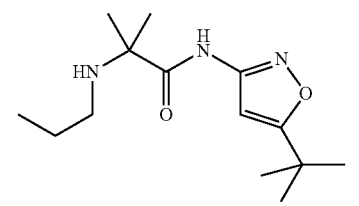 | N-(5-tert-Butyl-isoxazol-3-yl)-2-methyl-2-propylamino-propionamide |
| 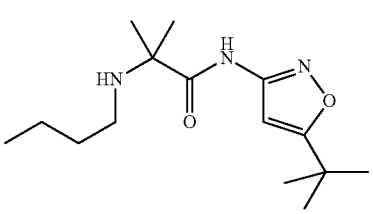 | 2-Butylamino-N-(5-tert-butyl-isoxazol-3-yl)-2-methyl-propionamide |
| 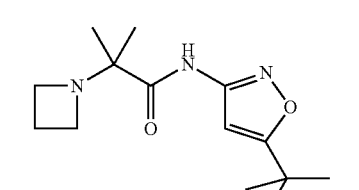 | 2-Azetidin-1-yl-N-(5-tert-butyl-isoxazol-3-yl)-isobutyramide |
| 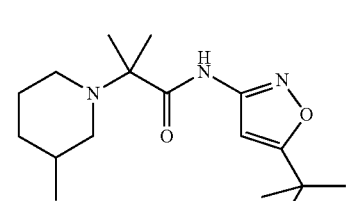 | N-(5-tert-Butyl-isoxazol-3-yl)-2-(3-methyl-piperidin-1-yl)-isobutyramide |
| 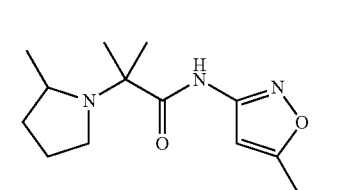 | N-(5-tert-Butyl-isoxazol-3-yl)-2-(2-methyl-pyrrolidin-1-yl)-isobutyramide |

TABLE II-continued

| | |
|---|---|
| 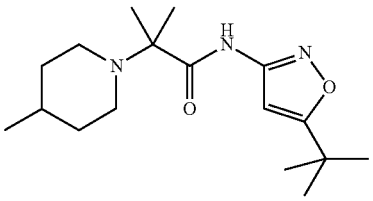 | N-(5-tert-Butyl-isoxazol-3-yl)-2-(4-methyl-piperidin-1-yl)-isobutyramide |
| 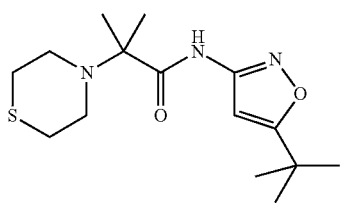 | N-(5-tert-Butyl-isoxazol-3-yl)-2-thiomorpholin-4-yl-isobutyramide |
| 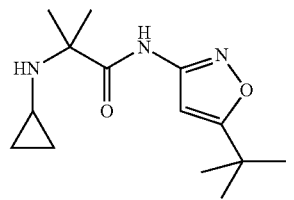 | N-(5-tert-Butyl-isoxazol-3-yl)-2-cyclopropylamino-2-methyl-propionamide |
| 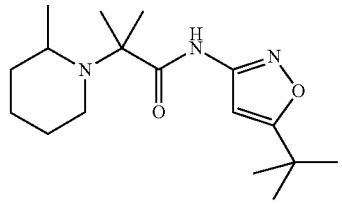 | N-(5-tert-Butyl-isoxazol-3-yl)-2-(2-methyl-piperidin-1-yl)-isobutyramide |
| 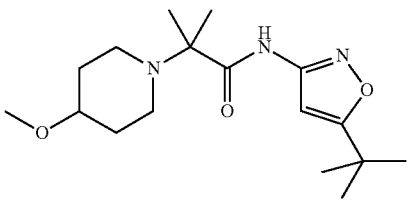 | N-(5-tert-Butyl-isoxazol-3-yl)-2-(4-methoxy-piperidin-1-yl)-isobutyramide |
| 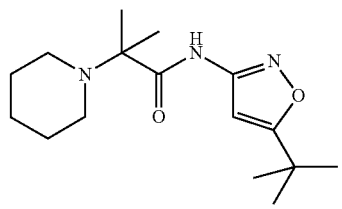 | N-(5-tert-Butyl-isoxazol-3-yl)-2-piperidin-1-yl-isobutyramide |
| 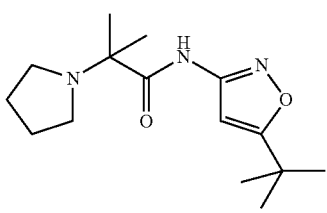 | N-(5-tert-Butyl-isoxazol-3-yl)-2-pyrrolidin-1-yl-isobutyramide |

TABLE II-continued

| Structure | Name |
|---|---|
| | N-(5-tert-Butyl-isoxazol-3-yl)-2-(4,4-difluoro-piperidin-1-yl)-isobutyramide |
| | 2-Cyclohexylamino-2-methyl-N-(5-trifluoromethyl-pyridin-2-yl)-propionamide |
| | 2-Azetidin-1-yl-N-(5-trifluoromethyl-pyridin-2-yl)-isobutyramide |
| | 2-Pyrrolidin-1-yl-N-(5-trifluoromethyl-pyridin-2-yl)-isobutyramide |
| | 2-Piperidin-1-yl-N-(5-trifluoromethyl-pyridin-2-yl)-isobutyramide |
| | 2-(Isopropyl-methyl-amino)-2-methyl-N-(5-trifluoromethyl-pyridin-2-yl)-propionamide |
| | 2-Isopropylamino-2-methyl-N-(5-trifluoromethyl-pyridin-2-yl)-propionamide |
| | N-(5-tert-Butyl-isoxazol-3-yl)-2-(5-chloro-indol-1-yl)-isobutyramide |

TABLE II-continued

| Structure | Name |
|---|---|
| | 2-(2-Aza-spiro[4.5]dec-2-yl)-N-(3-tert-butyl-isoxazol-5-yl)-isobutyramide |
| | N-(3-tert-Butyl-isoxazol-5-yl)-2-methyl-2-[(tetrahydro-pyran-4-ylmethyl)-amino]-propionamide |
| | N-(5-tert-Butyl-isoxazol-3-yl)-2-methyl-2-[(tetrahydro-pyran-4-ylmethyl)-amino]-propionamide |
| | N-(3-tert-Butyl-isoxazol-5-yl)-2-methyl-2-(tetrahydro-pyran-4-ylamino)-propionamide |
| | N-(5-tert-Butyl-isoxazol-3-yl)-2-methyl-2-(tetrahydro-pyran-4-ylamino)-propionamide |
| | 2-Methyl-N-(5-phenyl-2H-1,2,4-triazol-3-yl)-2-[(tetrahydro-pyran-4-ylmethyl)-amino]-propionamide |
| | 2-Methyl-N-(5-phenyl-2H-1,2,4-triazol-3-yl)-2-(tetrahydro-pyran-4-ylamino)-propionamide |
| | N-(5-tert-Butyl-isoxazol-3-yl)-2-(4-chloro-phenoxy)-2-methyl-propionamide |
| | N-(3-tert-Butyl-isoxazol-5-yl)-2-methyl-2-(tetrahydro-pyran-4-ylmethoxy)-propionamide |

TABLE II-continued

| Structure | Name |
|---|---|
| 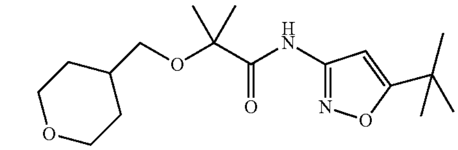 [SMILES: CC(C)(OCC1CCOCC1)C(=O)Nc1cc(C(C)(C)C)on1] | N-(5-tert-Butyl-isoxazol-3-yl)-2-methyl-2-(tetrahydro-pyran-4-ylmethoxy)-propionamide |
| 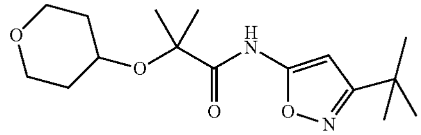 [SMILES: CC(C)(OC1CCOCC1)C(=O)Nc1cc(C(C)(C)C)no1] | N-(3-tert-Butyl-isoxazol-5-yl)-2-methyl-2-(tetrahydro-pyran-4-yloxy)-propionamide |
| 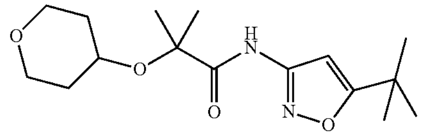 [SMILES: CC(C)(OC1CCOCC1)C(=O)Nc1cc(C(C)(C)C)on1] | N-(5-tert-Butyl-isoxazol-3-yl)-2-methyl-2-(tetrahydro-pyran-4-yloxy)-propionamide |
| 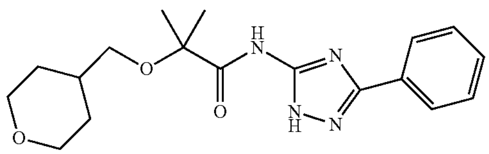 [SMILES: CC(C)(OCC1CCOCC1)C(=O)Nc1nc(-c2ccccc2)n[nH]1] | 2-Methyl-N-(5-phenyl-2H-1,2,4-triazol-3-yl)-2-(tetrahydro-pyran-4-ylmethoxy)-propponamide |
| 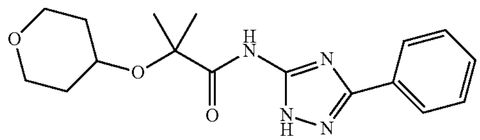 [SMILES: CC(C)(OC1CCOCC1)C(=O)Nc1nc(-c2ccccc2)n[nH]1] | 2-Methyl-N-(5-phenyl-2H-1,2,4-triazol-3-yl)-2-(tetrahydro-pyran-4-yloxy)-propionamide |
| 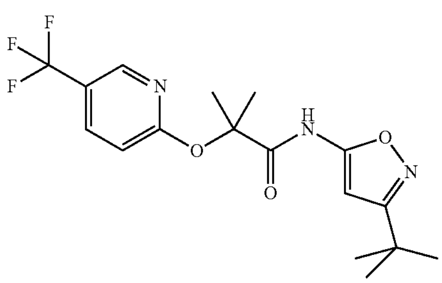 [SMILES: CC(C)(Oc1ccc(C(F)(F)F)cn1)C(=O)Nc1cc(C(C)(C)C)no1] | N-(3-tert-Butyl-isoxazol-5-yl)-2-methyl-2-(5-trifluoromethyl-pyridin-2-yloxy)-propionamide |
| 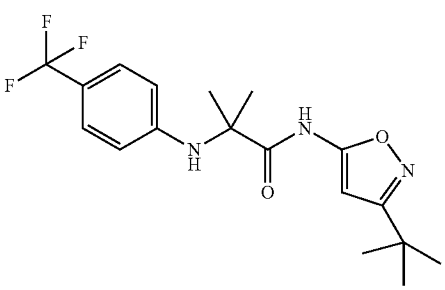 [SMILES: CC(C)(Nc1ccc(C(F)(F)F)cc1)C(=O)Nc1cc(C(C)(C)C)no1] | N-(3-tert-Butyl-isoxazol-5-yl)-2-methyl-2-(4-trifluoromethyl-phenylamino)-propionamide |
| 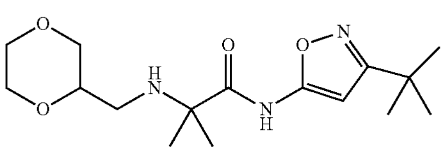 [SMILES: CC(C)(NCC1COCCO1)C(=O)Nc1cc(C(C)(C)C)no1] | N-(3-tert-Butyl-isoxazol-5-yl)-2-[([1,4]dioxan-2-ylmethyl)-amino]-2-methyl-propionamide |
| 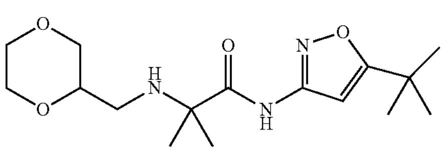 [SMILES: CC(C)(NCC1COCCO1)C(=O)Nc1cc(C(C)(C)C)on1] | N-(5-tert-Butyl-isoxazol-3-yl)-2-[([1,4]dioxan-2-ylmethyl)-amino]-2-methyl-propionamide |

TABLE II-continued

| Structure | Name |
|---|---|
| 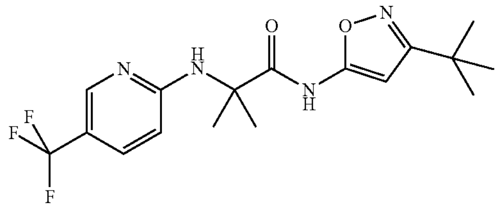 [SMILES: CC(C)(Nc1ccc(C(F)(F)F)cn1)C(=O)Nc1cc(C(C)(C)C)no1] | N-(3-tert-Butyl-isoxazol-5-yl)-2-methyl-2-(5-trifluoromethyl-pyridin-2-ylamino)-propionamide |
| 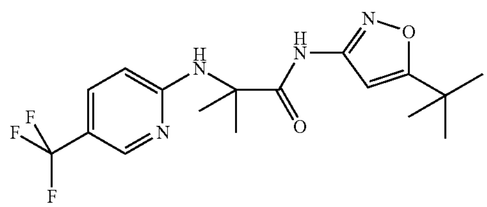 [SMILES: CC(C)(Nc1ccc(C(F)(F)F)cn1)C(=O)Nc1cc(C(C)(C)C)on1] | N-(5-tert-Butyl-isoxazol-3-yl)-2-methyl-2-(5-trifluoromethyl-pyridin-2-ylamino)-propionamide |
| 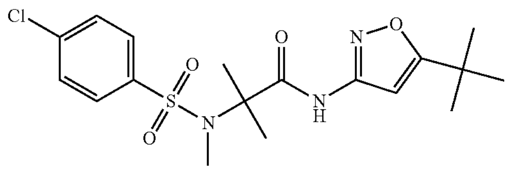 [SMILES: CN(C(C)(C)C(=O)Nc1cc(C(C)(C)C)on1)S(=O)(=O)c1ccc(Cl)cc1] | N-(5-tert-Butyl-isoxazol-3-yl)-2-[(4-chloro-benzenesulfonyl)-methyl-amino]-2-methyl-propionamide |
| 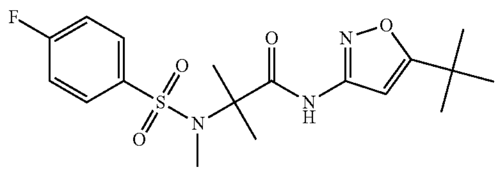 [SMILES: CN(C(C)(C)C(=O)Nc1cc(C(C)(C)C)on1)S(=O)(=O)c1ccc(F)cc1] | N-(5-tert-Butyl-isoxazol-3-yl)-2-[(4-fluoro-benzenesulfonyl)-methyl-amino]-2-methyl-propionamide |
| 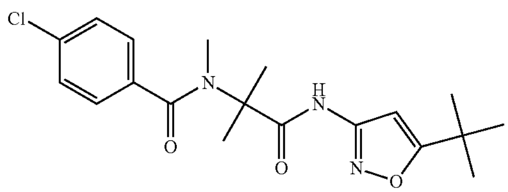 [SMILES: CN(C(=O)c1ccc(Cl)cc1)C(C)(C)C(=O)Nc1cc(C(C)(C)C)on1] | N-[1-(5-tert-Butyl-isoxazol-3-ylcarbamoyl)-1-methyl-ethyl]-4-chloro-N-methyl-benzamide |
| | 1,1-Dioxo-1λ6-thiomorpholine-4-carboxylic acid [1-(5-tert-butyl-isoxazol-3-ylcarbamoyl)-1-methyl-ethyl]-methyl-amide | or a pharmaceutically acceptable salt thereof.

Of the above compounds, the following are preferred CB2 agonists:

TABLE III

| Compound | CB2 EC50 (nM) |
|---|---|
| N-(5-tert-Butyl-isoxazol-3-yl)-2-(4-methoxy-phenylamino)-2-methyl-propionamide | 8.7 |
| N-(5-tert-Butyl-isoxazol-3-yl)-2-isopropylamino-2-methyl-propionamide | 100 |
| 2-sec-Butylamino-N-(5-tert-butyl-isoxazol-3-yl)-2-methyl-propionamide | 177 |
| N-(5-tert-Butyl-isoxazol-3-yl)-2-(isopropyl-methyl-amino)-2-methyl-propionamide | 8.4 |
| N-(5-tert-Butyl-isoxazol-3-yl)-2-morpholin-4-yl-isobutyramide | 45 |
| N-(5-tert-Butyl-isoxazol-3-yl)-2-cyclohexylamino-2-methyl-propionamide | 9.5 |

TABLE III-continued

| Compound | CB2 EC50 (nM) |
|---|---|
| 2-Butylamino-N-(5-tert-butyl-isoxazol-3-yl)-2-methyl-propionamide | 96 |
| N-(5-tert-Butyl-isoxazol-3-yl)-2-(3-methyl-piperidin-1-yl)-isobutyramide | 0.34 |
| N-(5-tert-Butyl-isoxazol-3-yl)-2-(2-methyl-pyrrolidin-1-yl)-isobutyramide | 24 |
| N-(5-tert-Butyl-isoxazol-3-yl)-2-(4-methyl-piperidin-1-yl)-isobutyramide | 2.6 |
| N-(5-tert-Butyl-isoxazol-3-yl)-2-thiomorpholin-4-yl-isobutyramide | 9.9 |
| N-(5-tert-Butyl-isoxazol-3-yl)-2-cyclopropylamino-2-methyl-propionamide | 235 |
| N-(5-tert-Butyl-isoxazol-3-yl)-2-(2-methyl-piperidin-1-yl)-isobutyramide | 1.2 |
| N-(5-tert-Butyl-isoxazol-3-yl)-2-(4-methoxy-piperidin-1-yl)-isobutyramide | 0.21 |
| N-(5-tert-Butyl-isoxazol-3-yl)-2-piperidin-1-yl-isobutyramide | 0.55 |
| N-(5-tert-Butyl-isoxazol-3-yl)-2-pyrrolidin-1-yl-isobutyramide | 23 |
| N-(5-tert-Butyl-isoxazol-3-yl)-2-(4,4-difluoro-piperidin-1-yl)-isobutyramide | 24 |
| 2-Cyclohexylamino-2-methyl-N-(5-trifluoromethyl-pyridin-2-yl)-propionamide | 469 |
| 2-Piperidin-1-yl-N-(5-trifluoromethyl-pyridin-2-yl)-isobutyramide | 127 |
| N-(5-tert-Butyl-isoxazol-3-yl)-2-(5-chloro-indol-1-yl)-isobutyramide | 0.22 |
| 2-(2-Aza-spiro[4.5]dec-2-yl)-N-(3-tert-butyl-isoxazol-5-yl)-isobutyramide | 0.45 |
| N-(3-tert-Butyl-isoxazol-5-yl)-2-methyl-2-[(tetrahydro-pyran-4-ylmethyl)-amino]-propionamide | 14 |
| N-(5-tert-Butyl-isoxazol-3-yl)-2-(4-chloro-phenoxy)-2-methyl-propionamide | 2.4 |
| N-(3-tert-Butyl-isoxazol-5-yl)-2-methyl-2-(tetrahydro-pyran-4-ylmethoxy)-propionamide | 8.1 |
| N-(5-tert-Butyl-isoxazol-3-yl)-2-methyl-2-[(tetrahydro-pyran-4-ylmethyl)-amino]-propionamide | 125 |
| N-(3-tert-Butyl-isoxazol-5-yl)-2-methyl-2-(tetrahydro-pyran-4-ylamino)-propionamide | 29 |
| N-(5-tert-Butyl-isoxazol-3-yl)-2-methyl-2-(tetrahydro-pyran-4-ylamino)-propionamide | 35 |
| 2-Methyl-N-(5-phenyl-2H-1,2,4-triazol-3-yl)-2-[(tetrahydro-pyran-4-ylmethyl)-amino]-propionamide | 98 |
| 2-Methyl-N-(5-phenyl-2H-1,2,4-triazol-3-yl)-2-(tetrahydro-pyran-4-ylamino)-propionamide | 260 |
| N-(3-tert-Butyl-isoxazol-5-yl)-2-methyl-2-(4-trifluoromethyl-phenylamino)-propionamide | 1.1 |
| N-(3-tert-Butyl-isoxazol-5-yl)-2-methyl-2-(5-trifluoromethyl-pyridin-2-ylamino)-propionamide | 0.78 |
| N-(5-tert-Butyl-isoxazol-3-yl)-2-methyl-2-(5-trifluoromethyl-pyridin-2-ylamino)-propionamide | 20 |
| N-(5-tert-Butyl-isoxazol-3-yl)-2-[(4-chloro-benzenesulfonyl)-methyl-amino]-2-methyl-propionamide | 0.36 |
| N-(5-tert-Butyl-isoxazol-3-yl)-2-[(4-fluoro-benzenesulfonyl)-methyl-amino]-2-methyl-propionamide | 0.13 |
| N-[1-(5-tert-Butyl-isoxazol-3-ylcarbamoyl)-1-methyl-ethyl]-4-chloro-N-methyl-benzamide | 124 |
| 1,1-Dioxo-1lambda*6*-thiomorpholine-4-carboxylic acid [1-(5-tert-butyl-isoxazol-3-ylcarbamoyl)-1-methyl-ethyl]-methyl-amide | 39 |
| N-(3-tert-Butyl-isoxazol-5-yl)-2-methyl-2-(tetrahydro-pyran-4-ylmethoxy)-propionamide | 8.1 |
| N-(5-tert-Butyl-isoxazol-3-yl)-2-methyl-2-(tetrahydro-pyran-4-ylmethoxy)-propionamide | 50 |
| N-(3-tert-Butyl-isoxazol-5-yl)-2-methyl-2-(tetrahydro-pyran-4-yloxy)-propionamide | 107 |
| N-(5-tert-Butyl-isoxazol-3-yl)-2-methyl-2-(tetrahydro-pyran-4-yloxy)-propionamide | 123 |
| 2-Methyl-N-(5-phenyl-2H-1,2,4-triazol-3-yl)-2-(tetrahydro-pyran-4-ylmethoxy)-propionamide | 51 |
| 2-Methyl-N-(5-phenyl-2H-1,2,4-triazol-3-yl)-2-(tetrahydro-pyran-4-yloxy)-propionamide | 235 |
| N-(3-tert-Butyl-isoxazol-5-yl)-2-methyl-2-(5-trifluoromethyl-pyridin-2-yloxy)-propionamide | 0.1 |

In all the compounds disclosed hereinabove in this application, in the event the nomenclature is in conflict with the structure, it shall be understood that the compound is defined by the structure.

The invention also relates to pharmaceutical preparations, containing as active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example azetidinyl, furanyl, pyranyl, benzoxazolyl, benzothiazolyl, benzimidazolyl, tetrahydropyranyl, dioxanyl, tetrahydrofuranyl, oxazolyl, isoxazolyl, oxadiazolyl, thiazolyl, isothiazolyl, pyrazolyl, pyrrolyl, imidazolyl, triazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, indolinyl, isoindolinyl, benzofuranyl, benzopyranyl and benzodioxolyl, or 2-aza-spiro[4.5]dec-2-yl, 1-aza-spiro[4.5]dec-1-yl, 1-aza-spiro[4.4]non-1-yl, 2-aza-spiro[4.4]non-2-yl, 2-aza-spiro[5.5]undec-2-yl, 1-aza-spiro[5.5]undec-1-yl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkylhio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —CH$_2$CHF$_2$, —CF$_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—$(C_1-C_4$ alkyl$)_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention also provides processes for making compounds of Formula (I) and Formula (II). Formula (III) can be made by the same schemes. In all Schemes, unless specified otherwise, $R^1$, $R^2$, $R^3$, $R^4$ and $R^5$ in the Formulas below shall have the meaning of $R^1$, $R^2$, $R^3$, $R^4$ and $R^5$ in Formula (I), Formula (II) and Formula (III) of the invention described herein above. Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization. The examples which follow are illustrative and, as recognized by one skilled in the art, particular reagents or conditions could be modified as needed for individual compounds without undue experimentation. Starting materials and intermediates used, in the Schemes below, are either commercially available or easily prepared from commercially available materials by those skilled in the art.

The compounds of Formula (II) may be synthesized according to Schemes 1 or 2 below:

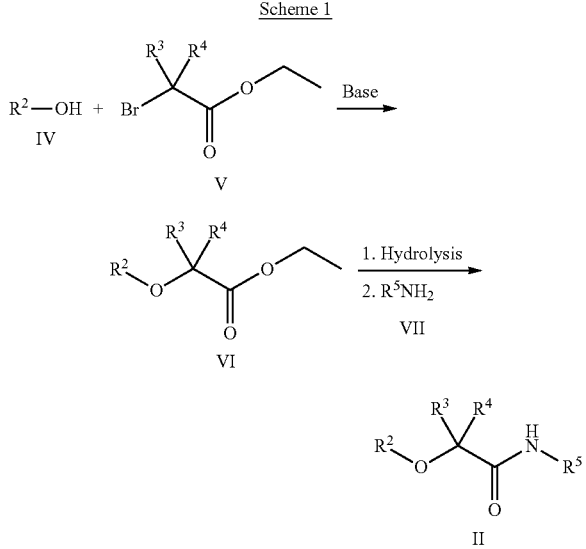

As illustrated in Scheme 1, reaction of a hydroxyl compound of Formula (IV) with a bromo-ester of Formula (V), in a suitable solvent, in the presence of a suitable base such as potassium hydroxide, provides a compound of Formula (VI). Hydrolysis of the ester of Formula (VI), in a suitable solvent using a suitable base, gives the corresponding acid. Reaction of this acid with reagents such as thionyl chloride or oxalyl chloride gives the corresponding acid chloride. Reaction of this acid chloride with an amine $R^5NH_2$ (VII), in a suitable solvent such as tetrahydrofuran, in the presence of a suitable base such as N,N-diisopropylethylamine, provides a compound of Formula (II).

Alternatively, the acid obtained above may also be coupled with the corresponding amine $R^5NH_2$(VII), under standard coupling conditions, to provide a compound of Formula (II). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine.

Compounds of Formula (II) may also be prepared as shown in Scheme 2.

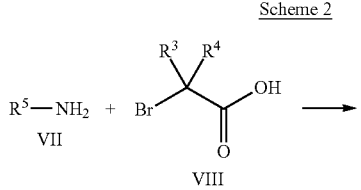

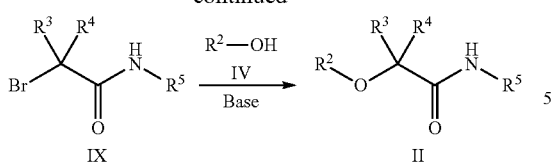

As illustrated in Scheme 2, reaction of an amine $R^5NH_2$ (VII) with a bromo acid of Formula (VIII) under conditions outlined in Scheme 1, provides an amide of Formula (IX). Reaction of the amide of Formula (IX) with a hydroxyl compound $R^2OH$ (IV), in a suitable solvent, in the presence of a suitable base such as sodium hydride, provides a compound of Formula (II).

Compounds of Formula (I) may be prepared according to Scheme 3.

Scheme 3

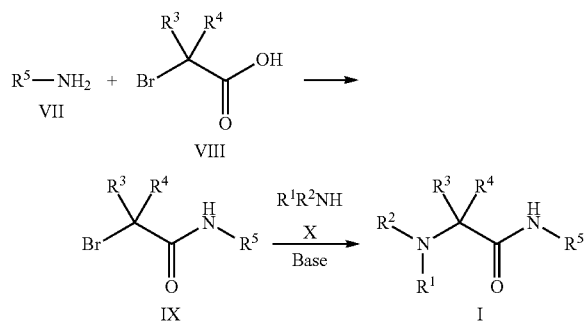

As illustrated in Scheme 3, reaction of an amine $R^5NH_2$ (VII) with a bromo acid of Formula (VIII) under conditions outlined in Scheme 1, provides an amide of Formula (IX). Reaction of the amide of Formula (IX) with an amine $R^1R^2NH(X)$, in a suitable solvent such as tetrahydrofuran, acetonitrile/water, dichloroethane, in the presence of a suitable base such as sodium hydride, cesium carbonate, N-methylmorpholine, provides a compound of Formula (I).

Compounds of Formula (III) may be synthesized by methods outlined in Schemes 1, 2 or 3.

Further modification of the initial product of Formula (I), Formula (II) and Formula (III) by methods known in the art and illustrated in the Examples below, may be used to prepare additional compounds of this invention.

Experimental Procedures Formula (II)
Method A

Synthesis of N-(5-tert-butyl-isoxazol-3-yl)-2-(4-chloro-phenoxy)-2-methyl-propionamide (Example 1 in Table 2)

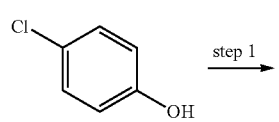

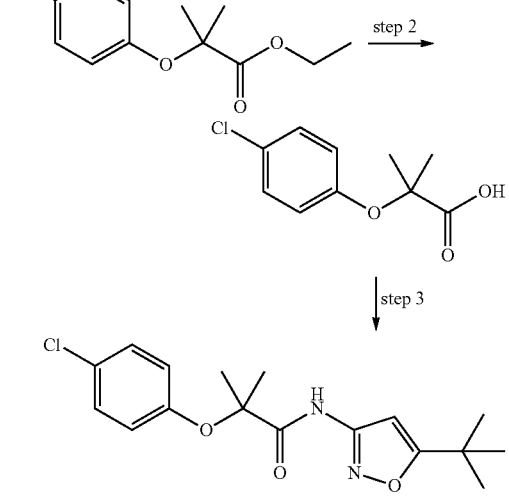

Step 1: Synthesis of 2-(4-chloro-phenoxy)-2-methyl-propionic acid ethyl ester To a solution of 4-chlorophenol (3 g, 23.3 mmol) in ethanol (100 mL) at room temperature is added potassium hydroxide (1.3 g, 23.3 mmol). The suspension is warmed at ~35° C. for 15 min to complete dissolution before ethyl α-bromoisobutyrate (3.46 mL, 23.3 mmol) is introduced. The reaction is then heated to reflux where it is maintained for 16 h. After this time, the mixture is cooled to room temperature and filtered. The collected solids are washed with additional ethanol (10 mL) and the combined filtrates are concentrated under reduced pressure. The residue is dissolved in DCM (60 mL) and washed with water (×2). The organic phase is dried ($Na_2SO_4$), filtered and concentrated under reduced pressure to provide the title compound as a clear colourless liquid (2.30 g, 40%). 1H NMR (400 MHz, CHLOROFORM-d): δ ppm 1.25 (3H, t, J=7.1 Hz), 1.58 (6H, s), 4.23 (2H, q, J=7.1 Hz), 6.78 (2H, d, J=9.0 Hz), 7.19 (2H, d, J=9.1 Hz); m/z: 243/245 [M+H$^+$].

Step 2: Synthesis of 2-(4-chloro-phenoxy)-2-methyl-propionic acid

To a solution of 2-(4-chloro-phenoxy)-2-methyl-propionic acid ethyl ester (2.0 g, 8.24 mmol) in tetrahydrofuran (16 mL) at room temperature is added water (4 mL) followed by lithium hydroxide monohydrate (0.69 g, 16.4 mmol). The reaction is stirred for 16 h at room temperature. After this time, the mixture is diluted with water and washed with DCM. The aqueous phase is separated, acidified to pH ~2 with 1M aqueous HCl solution and then extracted with DCM (×2). The combined organic extracts are washed with brine, dried (MgSO$_4$), filtered and concentrated under reduced pressure to give the title compound as a white solid (1.45 g, 82%). $^1$H NMR (400 MHz, CHLOROFORM-d): δ ppm 1.62 (6H, s), 6.89 (2H, d, J=9.0 Hz), 7.24 (2H, d, J=9.0 Hz).

Step 3 Amide Bond Formation: Synthesis of N-(5-tert-butyl-isoxazol-3-yl)-2-(4-chloro-phenoxy)-2-methyl-propionamide (Example 1 in Table 2)

To a solution of 2-(4-chloro-phenoxy)-2-methyl-propionic acid (0.20 g, 0.93 mmol) in DCM (3 mL) at room temperature under nitrogen is added thionyl chloride (0.41 mL, 5.58 mmol). The reaction is shaken for 16 h. After this time, the mixture is concentrated under reduced pressure and the crude material is used without further purification.

To a solution of 3-amino-5-tert-butyl isoxazole (78 mg, 0.57 mmol) in THF (3 mL) at room temperature is added the acid chloride (~0.46 mmol) followed by N,N-diisopropylethylamine (117 µL, 0.68 mmol). The resulting mixture is shaken for 16 h and then concentrated under reduced pressure. The residue is dissolved in DCM (3 mL) and then washed with saturated aqueous NaHCO$_3$ solution, dried (Na$_2$SO$_4$), filtered and concentrated under reduced pressure. Purification by preparative HPLC provided the title compound (35 mg, 23%).

Examples in Table 1, Method A are prepared according to a similar procedure.

Method B

Synthesis of N-(3-tert-Butyl-isoxazol-5-yl)-2-methyl-2-(tetrahydro-pyran-4-ylmethoxy)-propionamide (Example 2 in Table 2)

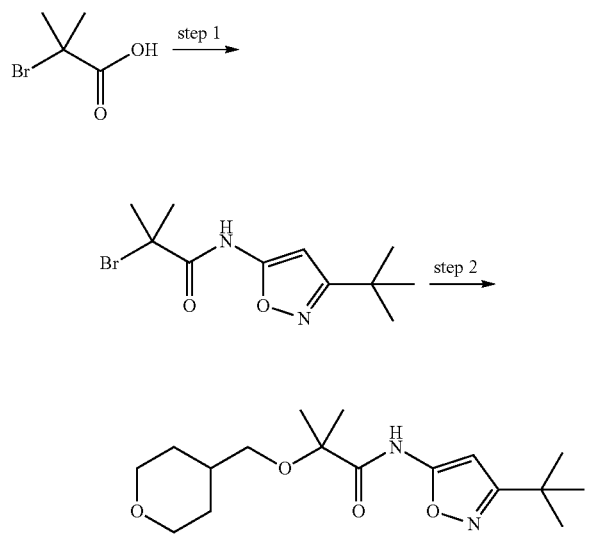

Step 1: Synthesis of 2-Bromo-N-(3-tert-butyl-isoxazol-5-yl)-2-methyl-propionamide To a flask containing 2-bromo-2-methyl-propionic acid (15.0 g, 89.8 mmol) in DCM (300 mL) under nitrogen are added DMF (0.5 mL) and oxalyl chloride (46.3 mL, 0.54 mol). The reaction mixture is stirred at room temperature for 16 h and then it is concentrated under reduced pressure. The crude acid chloride is redissolved in DCM (300 mL) N,N-diisopropylethylamine (46.9 mL, 0.27 mol) and 3-tert-butyl-isoxazol-5-ylamine (12.6 g, 89.8 mmol) are introduced. The reaction is stirred at room temperature for 16 h. After this time, the mixture is washed with saturated aqueous NaHCO$_3$ solution, brine and the organic layer is separated, dried (Na$_2$SO$_4$) and concentrated under reduced pressure. The crude product is purified by recrystallisation using heptanes/ isopropyl alcohol to give the title compound I(11.0 g, 43%). $^1$H NMR (400 MHz, CHLOROFORM-d) δ ppm 1.33 (9H, s), 2.04 (6H, s), 6.32 (1H, s), 9.05 (1H, br s).

According to this procedure the following amide is synthesised:

TABLE 1

| Structure | Name | Yield [%] | m/z [M + H$^+$] |
|---|---|---|---|
| ![structure] | 2-Bromo-2-methyl-N-(5-phenyl-4H-[1,2,4]triazol-3-yl)-propionamide | 39 | 309/311 |

Step 2: Synthesis of N-(3-tert-Butyl-isoxazol-5-yl)-2-methyl-2-(tetrahydro-pyran-4-ylmethoxy)-propionamide (Example 1 in Table 2)

To a solution of (tetrahydro-pyran-4-yl)-methanol (4 mL) at room temperature is added NaH (55 mg of a 60% dispersion in oil, 1.4 mmol). The reaction is warmed to 50° C. and stirred for 30 min. After this time, 2-bromo-N-(3-tert-butyl-isoxazol-5-yl)-2-methyl-propionamide (0.20 g, 0.69 mmol) is added and THF (2 mL) is introduced. The reaction is stirred at 60° C. for 5 h before it is quenched by the addition of methanol. The solvent is removed under reduced pressure and the crude residue that remains is purified by preparative HPLC to give the title compound (38 mg, 17%). m/z 289 [M+H$^+$].

Method B$^+$, Step 2: Synthesis of N-(3-tert-Butyl-isoxazol-5-yl)-2-methyl-2-(5-trifluoromethyl-pyridin-2-yloxy)-propionamide (Example 8)

To a solution of 2-bromo-N-(3-tert-butyl-isoxazol-5-yl)-2-methyl-propionamide (0.53 g, 1.78 mmol) and 5-trifluoromethyl-2-pyridinol (0.30 g, 1.84 mmol) in acetonitrile/water (95/5, 15 mL) is added silver (I) oxide (0.85 g, 3.68 mmol). The reaction is heated to 60° C. for 18 h. After cooling, the reaction mixture is filtered through a plug of Na$_2$SO$_4$/cotton wool. The filtrate is concentrated under reduced pressure to give a brown oil, which is triturated with heptanes/ethyl acetate to afford a grey powder. Further purification by column chromatography (silica, eluent heptanes, 2.5-20% ethyl acetate) afforded N-(3-tert-butyl-isoxazol-5-yl)-2-methyl-2-(5-trifluoromethyl-pyridin-2-yloxy)-propionamide as a white solid (33 mg, 5%). m/z 372 [M+H$^+$]

Examples in Table 2, Method B are prepared according to a similar procedure.

TABLE 2

Examples

| # | Structure | Name | m/z [M +H⁺] | Method |
|---|---|---|---|---|
| 1 | 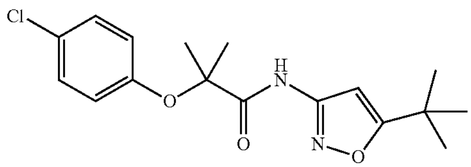 [SMILES: CC(C)(Oc1ccc(Cl)cc1)C(=O)Nc1cc(C(C)(C)C)on1] | N-(5-tert-Butyl-isoxazol-3-yl)-2-(4-chloro-phenoxy)-2-methyl-propionamide | 337/339 | A |
| 2 | 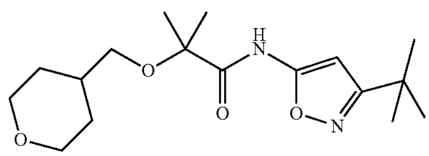 [SMILES: CC(C)(OCC1CCOCC1)C(=O)Nc1cc(C(C)(C)C)no1] | N-(3-tert-Butyl-isoxazol-5-yl)-2-methyl-2-(tetrahydro-pyran-4-ylmethoxy)-propionamide | 325 | B |
| 3 | 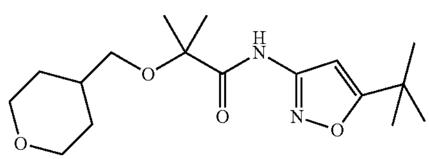 [SMILES: CC(C)(OCC1CCOCC1)C(=O)Nc1cc(C(C)(C)C)on1] | N-(5-tert-Butyl-isoxazol-3-yl)-2-methyl-2-(tetrahydro-pyran-4-ylmethoxy)-propionamide | 325 | B |
| 4 | 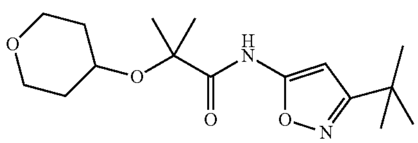 [SMILES: CC(C)(OC1CCOCC1)C(=O)Nc1cc(C(C)(C)C)no1] | N-(3-tert-Butyl-isoxazol-5-yl)-2-methyl-2-(tetrahydro-pyran-4-yloxy)-propionamide | 311 | B |
| 5 | 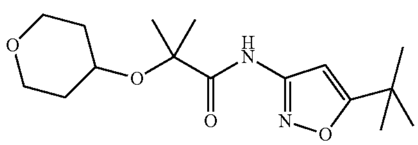 [SMILES: CC(C)(OC1CCOCC1)C(=O)Nc1cc(C(C)(C)C)on1] | N-(5-tert-Butyl-isoxazol-3-yl)-2-methyl-2-(tetrahydro-pyran-4-yloxy)-propionamide | 311 | B |
| 6 | 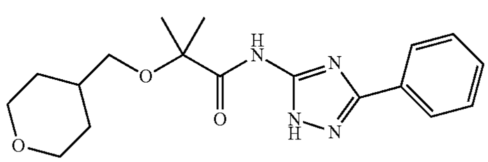 [SMILES: CC(C)(OCC1CCOCC1)C(=O)Nc1nc(-c2ccccc2)n[nH]1] | 2-Methyl-N-(5-phenyl-2H-1,2,4-triazol-3-yl)-2-(tetrahydro-pyran-4-ylmethoxy)-propionamide | 345 | B |
| 7 | 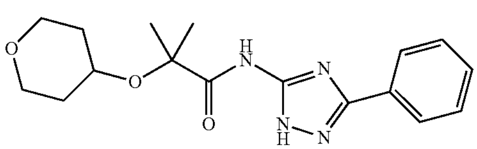 [SMILES: CC(C)(OC1CCOCC1)C(=O)Nc1nc(-c2ccccc2)n[nH]1] | 2-Methyl-N-(5-phenyl-2H-1,2,4-triazol-3-yl)-2-(tetrahydro-pyran-4-yloxy)-propionamide | 331 | B |
| 8 | 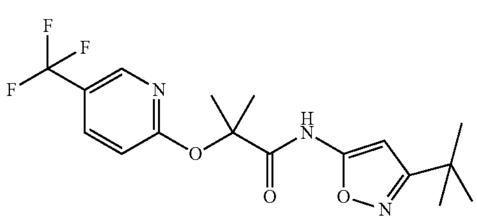 [SMILES: CC(C)(Oc1ccc(C(F)(F)F)cn1)C(=O)Nc1cc(C(C)(C)C)no1] | N-(3-tert-Butyl-isoxazol-5-yl)-2-methyl-2-(5-trifluoromethyl-pyridin-2-yloxy)-propionamide | 372 | B⁺ |

Experimental Procedures Formula (I)
Method C

Synthesis of 2-butylamino-N-(5-tert-butyl-isoxazol-3-yl)-2-methyl-propionamide (Example 17 in Table 4)

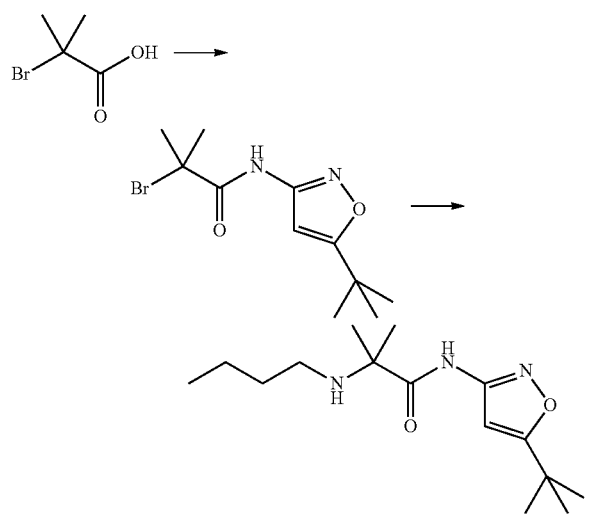

Step 1: Synthesis of 2-bromo-N-(5-tert-butyl-isoxazol-3-yl)-2-methyl-propionamide To a flask containing 2-bromo-2-methyl-propionic acid (5.0 g, 29.9 mmol) under nitrogen are added DMF (0.1 mL) and thionyl chloride (10 mL). The reaction mixture is heated to 60° C. where it is maintained for 2 h. After this time, the reaction is cooled to room temperature and concentrated under reduced pressure. The crude acid chloride is used without further purification.

To a solution of 3-amino-5-tert-butyl isoxazole (4.19 g, 29.9 mmol) and N,N-diisopropylamine (5.2 mL, 29.9 mmol) in DCM (20 mL) at room temperature is added the acid chloride (~29.9 mmol) as a solution in DCM (15 mL) dropwise. The reaction is stirred for 16 h. After this time, the mixture is washed with saturated aqueous NaHCO₃ solution (×2), brine and the organic layer is separated, dried (MgSO₄) and concentrated under reduced pressure. The crude product is purified by chromatography on silica eluting with 0% to 25% ethyl acetate/DCM to provide the title compound (8.49 g, 97%). m/z 289/291 [M+H⁺].

Using a similar procedure, the amides listed in Table 3 are synthesized.

TABLE 3

| Structure | Name | Yield [%] | m/z [M + H⁺] |
|---|---|---|---|
| 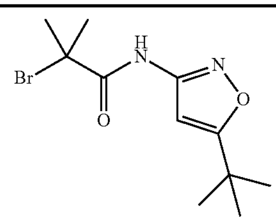 | 2-Bromo-N-(5-tert-butyl-isoxazol-3-yl)-2-methyl-propionamide | 97 | 289/291 |

TABLE 3-continued

| Structure | Name | Yield [%] | m/z [M + H⁺] |
|---|---|---|---|
| 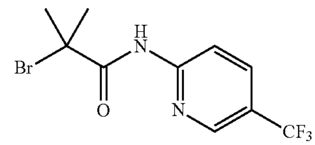 | 2-Bromo-2-methyl-N-(5-trifluoro-methyl-pyridin-2-yl)-propionamide | 42 | 311/313 |

Step 2: Synthesis of 2-butylamino-N-(5-tert-butyl-isoxazol-3-yl)-2-methyl-propionamide (Example 17 in Table 4)

To a solution of n-butylamine (51 mg, 0.69 mmol) in THF (2 mL) at room temperature under nitrogen is added NaH (33 mg, 1.38 mmol) in portions over 10 min. After the addition is complete, 2-bromo-N-(5-tert-butyl-isoxazol-3-yl)-2-methyl-propionamide (0.10 g, 0.35 mmol) is introduced to the reaction and the resulting mixture is stirred for 16 h. The solvent is then removed under reduced pressure and the residue is partitioned between DCM and saturated aqueous NaHCO₃ solution. The organic phase is separated, washed with brine, dried (MgSO₄), filtered and concentrated under reduced pressure. The crude product is purified by mass-triggered preparative HPLC. The purified compound is dissolved in DCM and free-based with Ambersep 900-OH resin over 2 h. After this time, the suspension is filtered and the filtrate is concentrated under reduced pressure to provide the title compound (35.4 mg, 37%).

Examples listed in Table 5, method C are prepared according to a similar procedure, with the following modifications noted: For examples 9 and 10 the reaction is performed at 80° C. and the purification step is achieved by chromatography on silica using DCM as the eluent. For examples 14-16, 18-22, 26, 36 the product is free-based using 1M aqueous NaOH solution after HPLC purification. For example 35 the purification step is achieved by chromatography on silica using heptanes and 20% DCM as the eluent. For examples 40-47, the reaction is heated to 50° C. until complete conversion. For example 36, 40, 43-45 the purification is performed by chromatography on silica using heptanes and 0-50% ethyl acetate as the eluent. Example 41-42 and 47 are purified by column chromatography (silica, eluent: heptanes, 0-50% ethyl acetate), followed by mass-triggered LC (neutral conditions). The hydrochloride salt of examples 40, 43, 45 and 46 is formed by trituration with 1M HCl solution in ether.

Examples listed in Table 4, method C are prepared according to this procedure

Method D

Synthesis of N-(5-tert-Butyl-isoxazol-3-yl)-2-methyl-2-[(tetrahydro-pyran-4-ylmethyl)-amino]-propionamide (Example 38, Table 4)

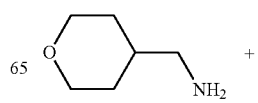

-continued

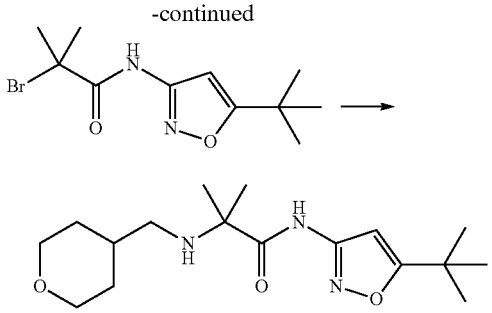

To a solution of 2-bromo-N-(3-tert-butyl-isoxazol-5-yl)-2-methyl-propionamide (0.25 g, 0.87 mmol, prepared according to method C, step 1)) and 1-tetrahydro-2H-pyran-4-yl-methane-amine (0.20 g, 1.73 mmol) in acetonitrile/water (95/5, 4 mL) is added silver (I) oxide (0.80 g, 3.68 mmol). The reaction is heated to 60° C. for 18 h. After cooling, the reaction mixture is filtered through a plug of Na₂SO₄/cotton wool. The filtrate is concentrated under reduced pressure to give a brown oil, which is purified by mass-triggered preparative LC (neutral conditions) to afford N-(5-tert-butyl-isoxazol-3-yl)-2-methyl-2-[(tetrahydro-pyran-4-ylmethyl)-amino]-propionamide (28 mg, 10%). m/z 324 [M+H⁺]. The hydrochloride salt of the title compound is formed by trituration with 1M HCl solution in ether.

Examples listed in Table 4, method D are prepared according to this procedure

Method E

Synthesis of N-(3-tert-Butyl-isoxazol-5-yl)-2-methyl-2-(tetrahydro-pyran-4-ylamino)-propionamide (Example 39, Table 4)

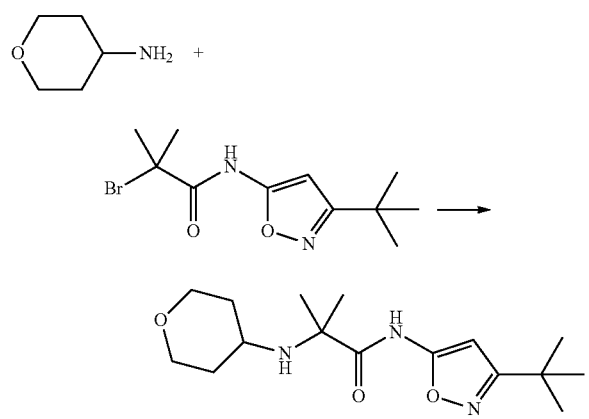

To a solution of 2-bromo-N-(3-tert-butyl-isoxazol-5-yl)-2-methyl-propionamide (prepared according to method B, step 1, 2.0 g, 6.92 mmol) in anhydrous THF (40 mL) are added 4-aminotetrahydropyran (0.70 g, 6.92 mmol) and Cs₂CO₃. The reaction is heated to 60° C. for 48 h. After cooling the reaction mixture is partitioned between DCM (100 mL) and water (100 mL). The organic layer is separated and dried over Na₂SO₄. Filtration and concentration of the filtrate gives a yellow oil. The oil is dissolved in DCM and extracted with 1M aqueous HCl solution. The acidic aqueous extract is basified with 5M aqueous NaOH solution and extracted with DCM (3×100 mL). The combined organic extracts are dried over Na₂SO₄, filtered and the filtrate is concentrated under reduced pressure to give N-(3-tert-butyl-isoxazol-5-yl)-2-methyl-2-(tetrahydro-pyran-4-ylamino)-propionamide (0.89 g, 42%). m/z 310 [M+H⁺]. Conversion into its hydrochloride salt is achieved upon treatment with 1M HCl solution in diethyl ether (2.89 mL).

Examples listed in Table 4, method E are prepared according to this procedure

Method F

Synthesis of N-(5-tert-Butyl-isoxazol-3-yl)-2-[(4-chloro-benzenesulfonyl)-methyl-amino]-2-methyl-propionamide (Example 48, Table 4)

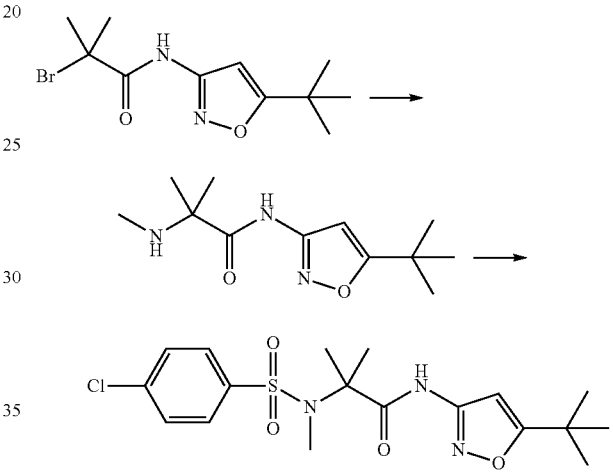

To a solution of 2-bromo-N-(3-tert-butyl-isoxazol-5-yl)-2-methyl-propionamide (prepared according to method B, step 1, 1.45 g, 1.5 mmol) in anhydrous dichloroethane (25 mL) are added methylamine hydrochloride (0.66 g, 10.0 mmol) and 1,8-diazabicyclo[5.40]undec-7-ene (3.81 g, 25.0 mmol). The reaction is heated to 85° C. for 16 h. After cooling the reaction mixture to ambient temperature it was washed with saturated NaHCO₃ (25 mL). The water layer was extracted with dichloromethane (25 mL). The combined organic layers were dried over MgSO₄, filtered and the filtrate is concentrated under reduced pressure. The crude product is purified by chromatography on silica eluting with 0% to 10% methanol/DCM to provide N-(3-tert-butyl-isoxazol-5-yl)-2-methylamino-2-methyl-propionamide (0.21 g, 17%). To a solution of N-(3-tert-butyl-isoxazol-5-yl)-2-methylamino-propionamide (36 mg, 0.15 mmol) in anhydrous dichloroethane (1 mL) are added N-methylmorpholine (82 μL, 0.75 mmol) and 4-chlorobenzenesulfonyl chloride (63 mg, 0.30 mmol). The reaction is concentrated under reduced pressure to give a yellow oil, which is purified by mass-triggered preparative HPLC to afford N-(5-tert-Butyl-isoxazol-3-yl)-2-[(4-chloro-benzenesulfonyl)-methyl-amino]-2-methyl-propionamide (32 mg, 52%). m/z 414 [M+H⁺]

Examples listed in Table 4, method F are prepared according to this procedure.

TABLE 4

Examples

| # | Structure | Name | m/z [M + H+] | Method |
|---|---|---|---|---|
| 9 | 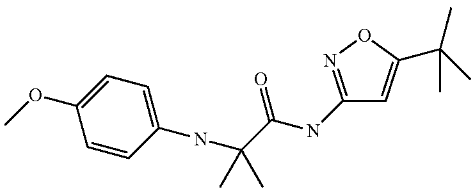 [SMILES: COc1ccc(NC(C)(C)C(=O)Nc2cc(C(C)(C)C)on2)cc1] | N-(5-tert-Butyl-isoxazol-3-yl)-2-(4-methoxy-phenylamino)-2-methyl-propionamide | 332 | C |
| 10 | 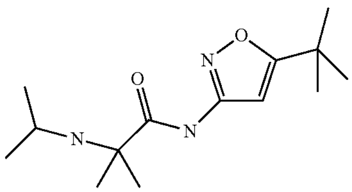 [SMILES: CC(C)NC(C)(C)C(=O)Nc1cc(C(C)(C)C)on1] | N-(5-tert-Butyl-isoxazol-3-yl)-2-isopropylamino-2-methyl-propionamide | 268 | C |
| 11 | 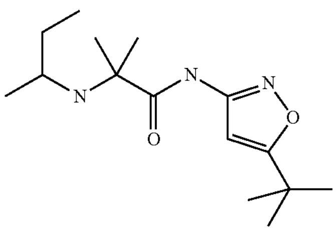 [SMILES: CCC(C)NC(C)(C)C(=O)Nc1cc(C(C)(C)C)on1] | 2-sec-Butylamino-N-(5-tert-butyl-isoxazol-3-yl)-2-methyl-propionamide | 282 | C |
| 12 | 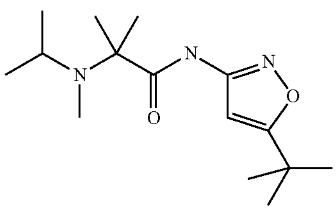 [SMILES: CC(C)N(C)C(C)(C)C(=O)Nc1cc(C(C)(C)C)on1] | N-(5-tert-Butyl-isoxazol-3-yl)-2-(isopropyl-methyl-amino)-2-methyl-propionamide | 282 | C |
| 13 | 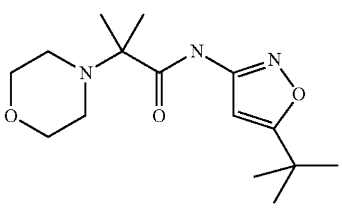 [SMILES: CC(C)(C)c1cc(NC(=O)C(C)(C)N2CCOCC2)no1] | N-(5-tert-Butyl-isoxazol-3-yl)-2-morpholin-4-yl-isobutyramide | 296 | C |
| 14 | 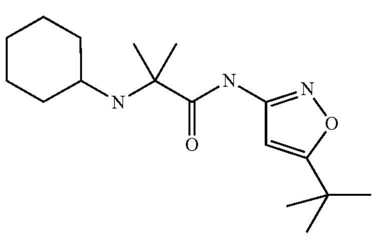 [SMILES: CC(C)(NC1CCCCC1)C(=O)Nc1cc(C(C)(C)C)on1] | N-(5-tert-Butyl-isoxazol-3-yl)-2-cyclohexylamino-2-methyl-propionamide | 308 | C |
| 15 | 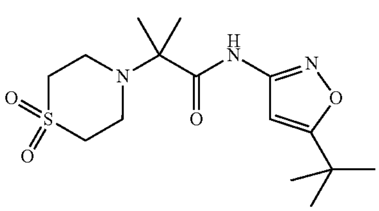 [SMILES: CC(C)(C)c1cc(NC(=O)C(C)(C)N2CCS(=O)(=O)CC2)no1] | N-(5-tert-Butyl-isoxazol-3-yl)-2-(1,1-dioxo-1□6-thiomorpholin-4-yl)-isobutyramide | 344 | C |

TABLE 4-continued

Examples

| # | Structure | Name | m/z [M + H+] | Method |
|---|---|---|---|---|
| 16 | 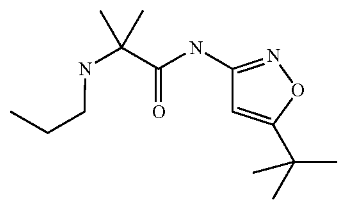 [SMILES: CCCNC(C)(C)C(=O)Nc1cc(C(C)(C)C)on1] | N-(5-tert-Butyl-isoxazol-3-yl)-2-methyl-2-propylamino-propionamide | 268 | C |
| 17 | 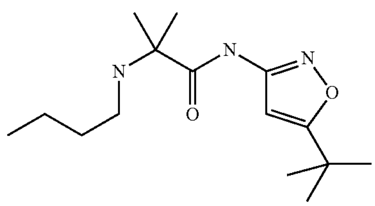 [SMILES: CCCCNC(C)(C)C(=O)Nc1cc(C(C)(C)C)on1] | 2-Butylamino-N-(5-tert-butyl-isoxazol-3-yl)-2-methyl-propionamide | 282 | C |
| 18 | 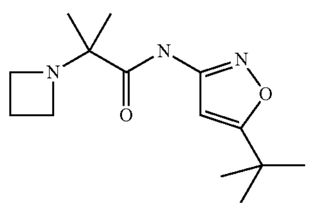 [SMILES: CC(C)(C)c1cc(NC(=O)C(C)(C)N2CCC2)no1] | 2-Azetidin-1-yl-N-(5-tert-butyl-isoxazol-3-yl)-isobutyramide | 266 | C |
| 19 | 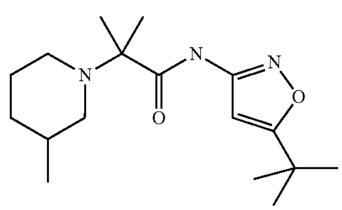 [SMILES: CC1CCCN(C(C)(C)C(=O)Nc2cc(C(C)(C)C)on2)C1] | N-(5-tert-Butyl-isoxazol-3-yl)-2-(3-methyl-piperidin-1-yl)-isobutyramide | 308 | C |
| 20 | 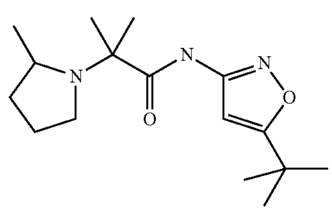 [SMILES: CC1CCCN1C(C)(C)C(=O)Nc1cc(C(C)(C)C)on1] | N-(5-tert-Butyl-isoxazol-3-yl)-2-(2-methyl-pyrrolidin-1-yl)-isobutyramide | 294 | C |
| 21 | 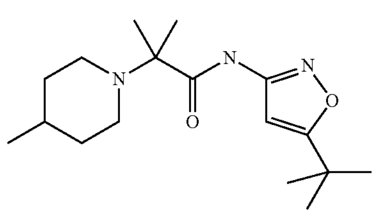 [SMILES: CC1CCN(C(C)(C)C(=O)Nc2cc(C(C)(C)C)on2)CC1] | N-(5-tert-Butyl-isoxazol-3-yl)-2-(4-methyl-piperidin-1-yl)-isobutyramide | 308 | C |
| 22 | 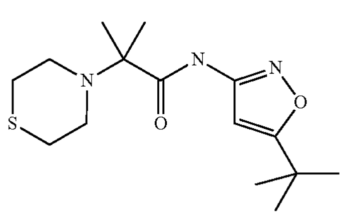 [SMILES: CC(C)(C)c1cc(NC(=O)C(C)(C)N2CCSCC2)no1] | N-(5-tert-Butyl-isoxazol-3-yl)-2-thiomorpholin-4-yl-isobutyramide | 312 | C |

TABLE 4-continued

Examples

| # | Structure | Name | m/z [M + H+] | Method |
|---|---|---|---|---|
| 23 | 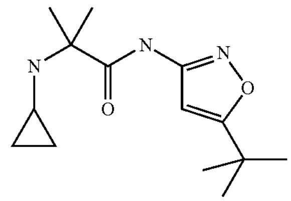 [SMILES: CC(C)(NC1CC1)C(=O)Nc1cc(C(C)(C)C)on1] | N-(5-tert-Butyl-isoxazol-3-yl)-2-cyclopropylamino-2-methyl-propionamide | 266 | C |
| 24 | 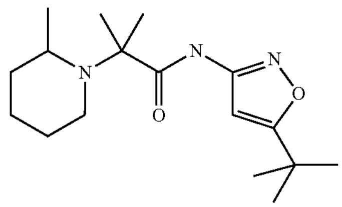 [SMILES: CC1CCCCN1C(C)(C)C(=O)Nc1cc(C(C)(C)C)on1] | N-(5-tert-Butyl-isoxazol-3-yl)-2-(2-methyl-piperidin-1-yl)-isobutyramide | 308 | C |
| 25 | 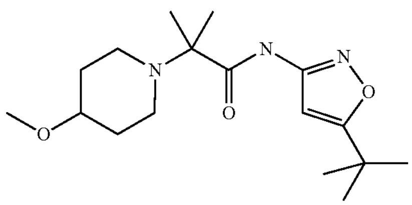 [SMILES: COC1CCN(C(C)(C)C(=O)Nc2cc(C(C)(C)C)on2)CC1] | N-(5-tert-Butyl-isoxazol-3-yl)-2-(4-methoxy-piperidin-1-yl)-isobutyramide | 324 | C |
| 26 | 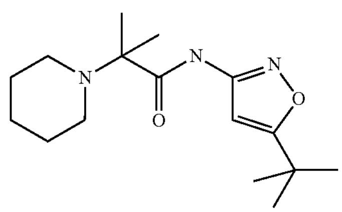 [SMILES: CC(C)(C)c1cc(NC(=O)C(C)(C)N2CCCCC2)no1] | N-(5-tert-Butyl-isoxazol-3-yl)-2-piperidin-1-yl-isobutyramide | 294 | C |
| 27 | 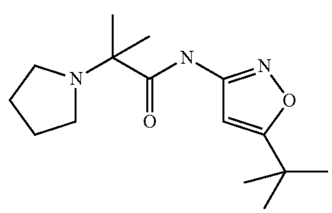 [SMILES: CC(C)(C)c1cc(NC(=O)C(C)(C)N2CCCC2)no1] | N-(5-tert-Butyl-isoxazol-3-yl)-2-pyrrolidin-1-yl-isobutyramide | 280 | C |
| 28 | 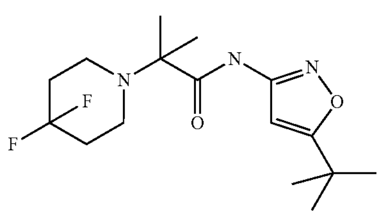 | N-(5-tert-Butyl-isoxazol-3-yl)-2-(4,4-difluoro-piperidin-1-yl)-isobutyramide | 330 | C |
| 29 | 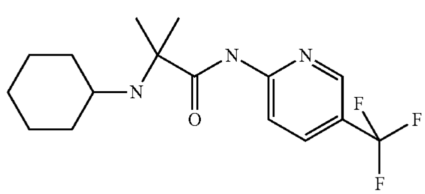 [SMILES: CC(C)(NC1CCCCC1)C(=O)Nc1ccc(C(F)(F)F)cn1] | 2-Cyclohexylamino-2-methyl-N-(5-trifluoromethyl-pyridin-2-yl)-propionamide | 330 | C |

TABLE 4-continued

| # | Structure | Name | m/z [M + H⁺] | Method |
|---|---|---|---|---|
| 30 | 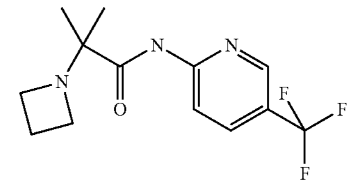 [SMILES: CC(C)(C(=O)Nc1ccc(C(F)(F)F)cn1)N1CCC1] | 2-Azetidin-1-yl-N-(5-trifluoromethyl-pyridin-2-yl)-isobutyramide | 288 | C |
| 31 | 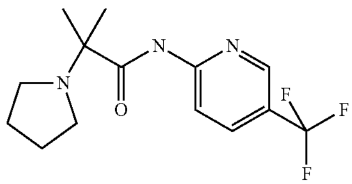 [SMILES: CC(C)(C(=O)Nc1ccc(C(F)(F)F)cn1)N1CCCC1] | 2-Pyrrolidin-1-yl-N-(5-trifluoromethyl-pyridin-2-yl)-isobutyramide | 302 | C |
| 32 | 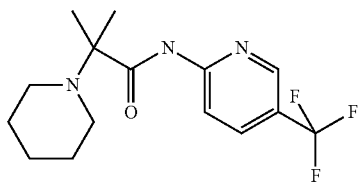 [SMILES: CC(C)(C(=O)Nc1ccc(C(F)(F)F)cn1)N1CCCCC1] | 2-Piperidin-1-yl-N-(5-trifluoromethyl-pyridin-2-yl)-isobutyramide | 316 | C |
| 33 | 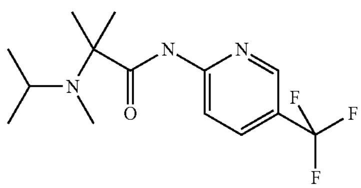 [SMILES: CC(C)N(C)C(C)(C)C(=O)Nc1ccc(C(F)(F)F)cn1] | 2-(Isopropyl-methyl-amino)-2-methyl-N-(5-trifluoromethyl-pyridin-2-yl)-propionamide | 304 | C |
| 34 | 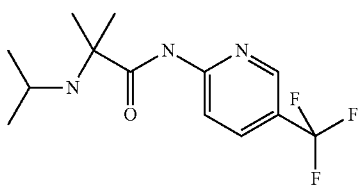 [SMILES: CC(C)NC(C)(C)C(=O)Nc1ccc(C(F)(F)F)cn1] | 2-Isopropylamino-2-methyl-N-(5-trifluoromethyl-pyridin-2-yl)-propionamide | 290 | C |
| 35 | 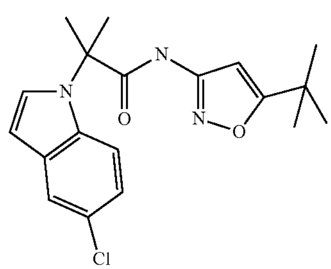 [SMILES: CC(C)(C)c1cc(NC(=O)C(C)(C)n2ccc3cc(Cl)ccc32)no1] | N-(5-tert-Butyl-isoxazol-3-yl)-2-(5-chloro-indol-1-yl)-isobutyramide | 360/362 | C |
| 36 | 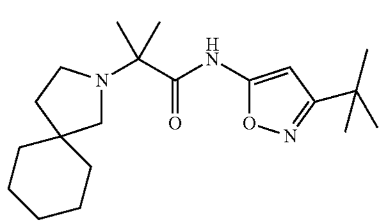 [SMILES: CC(C)(C)c1cc(NC(=O)C(C)(C)N2CCC3(CCCCC3)C2)on1] | 2-(2-Aza-spiro[4.5]dec-2-yl)-N-(3-tert-butyl-isoxazol-5-yl)-isobutyramide | 348 | C |

TABLE 4-continued

Examples

| # | Structure | Name | m/z [M + H+] | Method |
|---|---|---|---|---|
| 37 | 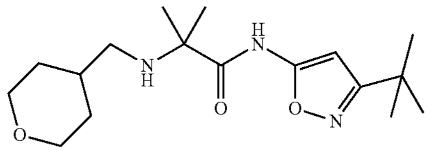 [SMILES: CC(C)(NCC1CCOCC1)C(=O)Nc1cc(C(C)(C)C)no1] | N-(3-tert-Butyl-isoxazol-5-yl)-2-methyl-2-[tetrahydro-pyran-4-ylmethyl)-amino]-propionamide | 324 | C |
| 38 | 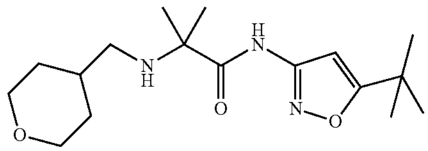 [SMILES: CC(C)(NCC1CCOCC1)C(=O)Nc1cc(C(C)(C)C)on1] | N-(5-tert-Butyl-isoxazol-3-yl)-2-methyl-2-[(tetrahydro-pyran-4-ylmethyl)-amino]-propionamide | 324 | D |
| 39 | 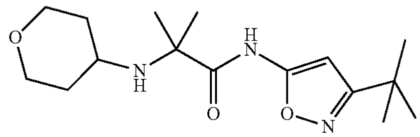 [SMILES: CC(C)(NC1CCOCC1)C(=O)Nc1cc(C(C)(C)C)no1] | N-(3-tert-Butyl-isoxazol-5-yl)-2-methyl-2-(tetrahydro-pyran-4-ylamino)-propionamide | 310 | E |
| 40 | 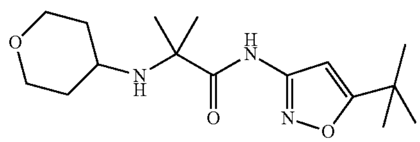 | N-(5-tert-Butyl-isoxazol-3-yl)-2-methyl-2-(tetrahydro-pyran-4-ylamino)-propionamide | 310 | C |
| 41 | 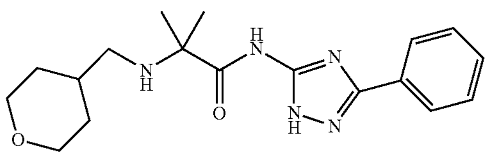 [SMILES: CC(C)(NCC1CCOCC1)C(=O)Nc1nc(-c2ccccc2)n[nH]1] | 2-Methyl-N-(5-phenyl-2H-1,2,4-triazol-3-yl)-2-[(tetrahydro-pyran-4-ylmethyl)-amino]-propionamide | 344 | C |
| 42 | 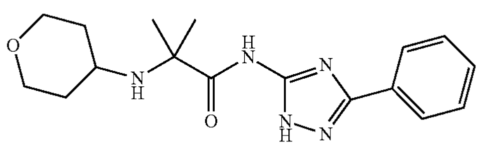 [SMILES: CC(C)(NC1CCOCC1)C(=O)Nc1nc(-c2ccccc2)n[nH]1] | 2-Methyl-N-(5-phenyl-2H-1,2,4-triazol-3-yl)-2-(tetrahydro-pyran-4-ylamino)-propionamide | 330 | C |
| 43 | 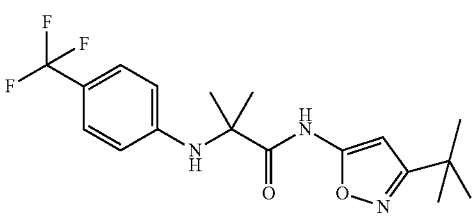 [SMILES: CC(C)(Nc1ccc(C(F)(F)F)cc1)C(=O)Nc1cc(C(C)(C)C)no1] | N-(3-tert-Butyl-isoxazol-5-yl)-2-methyl-2-(4-trifluoromethyl-phenylamino)-propionamide | 370 | C |
| 44 | 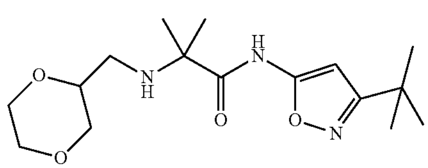 [SMILES: CC(C)(NCC1COCCO1)C(=O)Nc1cc(C(C)(C)C)no1] | N-(3-tert-Butyl-isoxazol-5-yl)-2-[([1,4]dioxan-2-ylmethyl)-amino]-2-methyl-propionamide 326 | 326 | C |
| 45 | 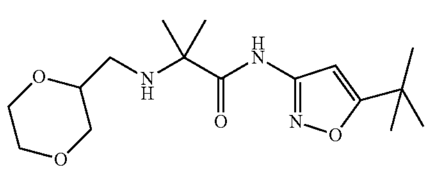 [SMILES: CC(C)(NCC1COCCO1)C(=O)Nc1cc(C(C)(C)C)on1] | N-(5-tert-Butyl-isoxazol-3-yl)-2-[([1,4]dioxan-2-ylmethyl)-amino]-2-methyl-propionamide | 326 | C |

TABLE 4-continued

Examples

| # | Structure | Name | m/z [M + H+] | Method |
|---|---|---|---|---|
| 46 | 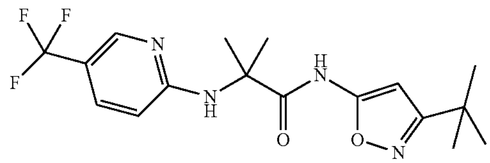 [SMILES: CC(C)(Nc1ccc(C(F)(F)F)cn1)C(=O)Nc1cc(C(C)(C)C)no1] | N-(3-tert-Butyl-isoxazol-5-yl)-2-methyl-2-(5-trifluoromethyl-pyridin-2-ylamino)-propionamide | 371 | C |
| 47 | 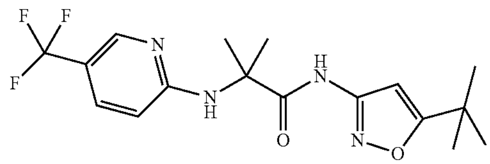 [SMILES: CC(C)(Nc1ccc(C(F)(F)F)cn1)C(=O)Nc1cc(C(C)(C)C)on1] | N-(5-tert-Butyl-isoxazol-3-yl)-2-methyl-2-(5-trifluoromethyl-pyridin-2-ylamino)-propionamide | 371 | C |
| 48 | 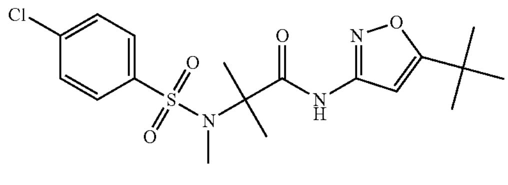 [SMILES: CN(C(C)(C)C(=O)Nc1cc(C(C)(C)C)on1)S(=O)(=O)c1ccc(Cl)cc1] | N-(5-tert-Butyl-isoxazol-3-yl)-2-[(4-chloro-benzenesulfonyl)-methyl-amino]-2-methyl-propionamide | 414 | F |
| 49 | 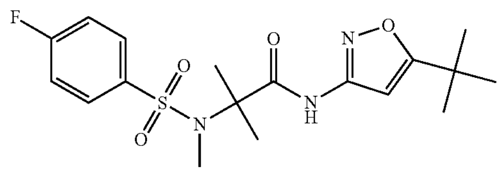 [SMILES: CN(C(C)(C)C(=O)Nc1cc(C(C)(C)C)on1)S(=O)(=O)c1ccc(F)cc1] | N-(5-tert-Butyl-isoxazol-3-yl)-2-[(4-fluoro-benzenesulfonyl)-methyl-amino]-2-methyl-propionamide | 398 | F |
| 50 | 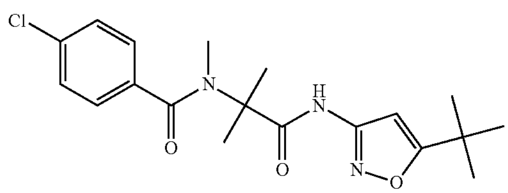 [SMILES: CN(C(=O)c1ccc(Cl)cc1)C(C)(C)C(=O)Nc1cc(C(C)(C)C)on1] | N-[1-(5-tert-Butyl-isoxazol-3-ylcarbamoyl)-1-methyl-ethyl]-4-chloro-N-methyl-benzamide | 379 | F |
| 51 | 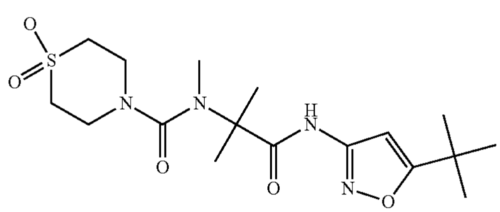 | 1,1-Dioxo-1$\lambda$6-thiomorpholine-4-carboxylic acid [1-(5-tert-butyl-isoxazol-3-ylcarbamoyl)-1-methyl-ethyl]-methyl-amide | 401 | F |

Assessment of Biological Properties

The biological properties of the compounds of the formula I, II and III were assessed using the assays described below.

A. Human CB1 and CB2 Receptor Binding:

Experimental Method:

CB2 membranes were purchased and made from HEK293 EBNA cells stably transfected with human CB2 receptor cDNA (Perkin Elmer Life and Analytical Sciences). CB1 membranes were isolated from HEK cells stably co-transfected with human CB1 receptor and Gcc16 cDNA's. The membrane preparation was bound to scintillation beads (Ysi-Poly-L-lysine SPA beads, GE Healthcare) for 4 hours at room temperature in assay buffer containing 50 mM Tris, pH 7.5, 2.5 mM EDTA, 5 mM $MgCl_2$, 0.8% fatty acid free Bovine Serum Albumin. Unbound membrane was removed by washing in assay buffer. Membrane-bead mixture was added to 96-well assay plates in the amounts of 15 ug membrane per well (CB2) or 2.5 ug per well (CB1) and 1 mg SPA bead per well. Compounds were added to the membrane-bead mixture in dose-response concentrations ranging from $1\times10^{-5}$M to $1\times10^{-10}$ M with 0.25% DMSO, final. The competition reaction was initiated with the addition of $^3$H-CP55940 (Perkin Elmer Life and Analytical Sciences) at a final concentration of 1.5 nM (CB2) or 2.5 nM (CB1). The reaction was incubated at room temperature for 18 hours and read on TopCount NXT plate reader. Total and non-specific binding was determined in the absence and presence of 1.25 uM Win 55212 (Sigma). 1050 values for each compound were calculated as the concentration of compound that inhibits the specific binding of the radioactively labeled ligand to the receptor by 50% using the XLFit 4.1 four parameter logistic model. 1050 values were converted to inhibition constant (Ki) values using Cheng-Prusoff equation.

B. CB2R Mediated Modulation of cAMP Synthesis:

Compounds of the invention were evaluated for their CB2 agonist or inverse agonistic activity in accordance with the following experimental method. Compounds which were shown to bind to CB2 by the binding assay described above but which were not shown to exhibit CB2R-mediated modulation of cAMP synthesis by this assay were presumed to be CB2 antagonists.

Experimental Method:

CHO cells expressing human CB2R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

C. CB1R Mediated Modulation of cAMP Synthesis:

Compounds of the invention were evaluated for their CB1 agonist or inverse agonistic activity in accordance with the following experimental method. Compounds which were shown to bind to CB1 by the binding assay described above but which were not shown to exhibit CB1R-mediated modulation of cAMP synthesis by this assay were presumed to be CB1 antagonists.

Experimental Method:

CHO cells expressing human CB1R (Euroscreen) were plated at a density of 5000 cells per well in 384 well plates and incubated overnight at 37° C. After removing the media, the cells were treated with test compounds diluted in stimulation buffer containing 1 mM IBMX, 0.25% BSA and 10 uM Forskolin. The assay was incubated for 30 minutes at 37° C. Cells were lysed and the cAMP concentration was measured using DiscoverX-XS cAMP kit, following the manufacturer's protocol. In this setting, agonists will decrease forskolin induced production of cAMP while inverse agonists will further increase forskolin induced production of cAMP. EC50 of agonists were calculated as follows. The maximal amount of cAMP produced by forskolin compared to the level of cAMP inhibited by 1 uM CP55940 is defined as 100%. The EC50 value of each test compound was determined as the concentration at which 50% of the forskolin-stimulated cAMP synthesis was inhibited. Data was analyzed using a four-parameter logistic model. (Model 205 of XLfit 4.0).

Compounds Having Agonist Activity

Through the use of the above described assays compounds were found to exhibit agonistic activity and thus to be particularly well suited for the treatment of pain as well as for the treatment of inflammation.

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, post-operative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lympho sarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hypergiycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: *The Science and Practice of Pharmacy*, 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Ass'n, 2000; H. C. Ansel and N. G. Popovish, *Pharmaceutical Dosage Forms and Drug Delivery Systems*, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:
1. A compound of the formula (III)

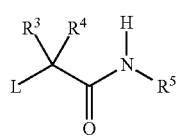

wherein for the formula (III)

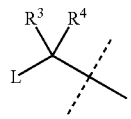

is chosen independently from members of column A in Table I, and

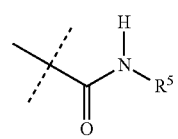

is chosen independently from members of column B in Table I:

TABLE I-continued
| A | B |
|---|---|
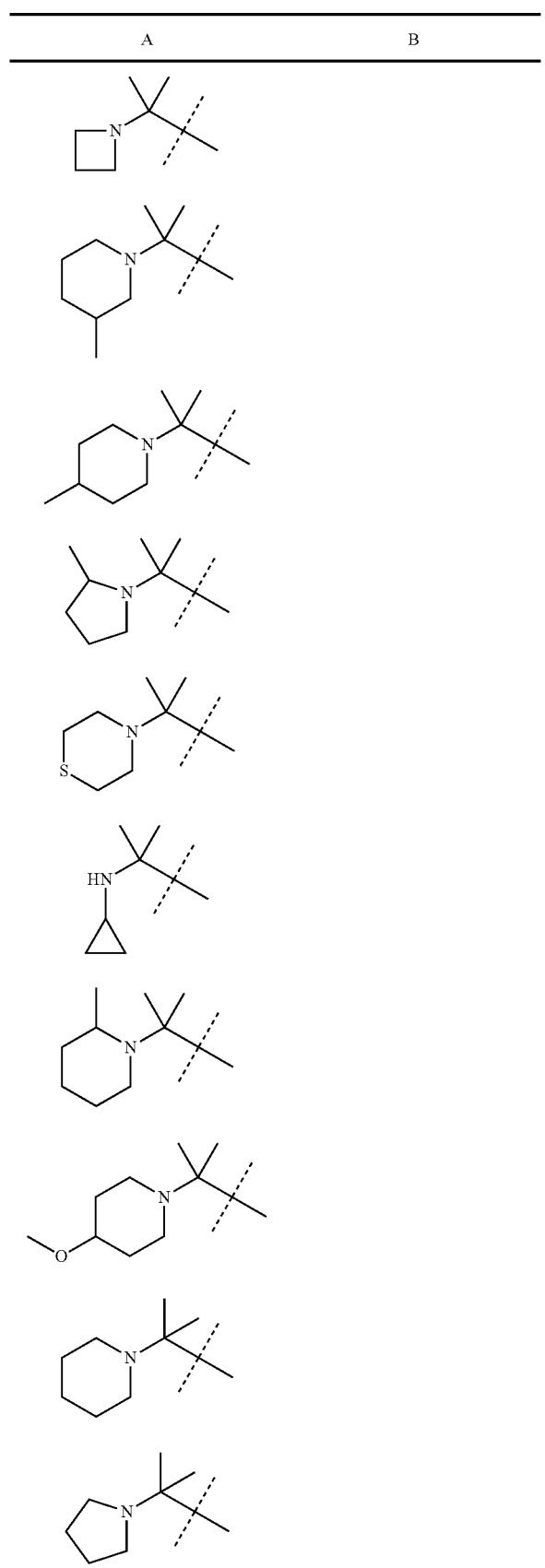
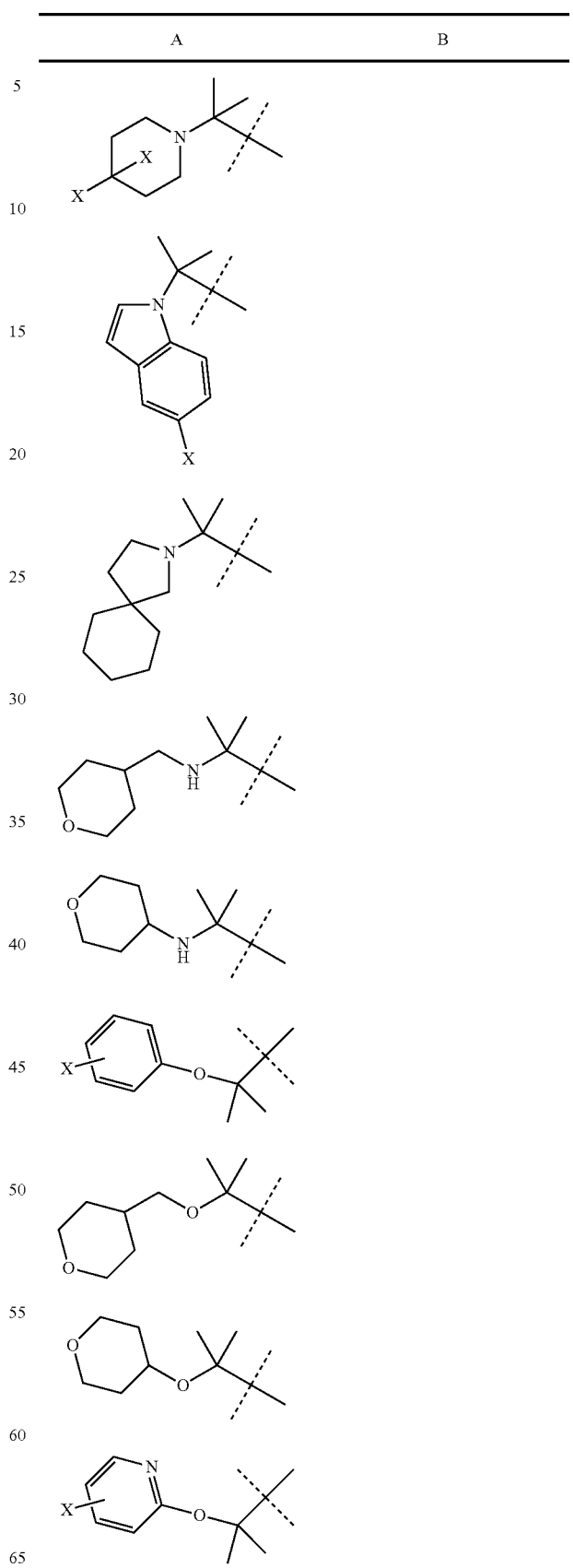

TABLE I-continued

| A | B |
|---|---|
| (substituted phenyl)-NH-C(CH₃)₂- structure | |
| 1,3-dioxane-CH₂-NH-C(CH₃)₂- structure | |
| (substituted pyridinyl)-NH-C(CH₃)₂- structure | |
| (substituted phenyl)-SO₂-N(CH₃)-C(CH₃)₂- structure | |
| (substituted phenyl)-C(O)-N(CH₃)-C(CH₃)₂- structure | |
| (1,1-dioxo-thiomorpholin-4-yl)-C(O)-N(CH₃)-C(CH₃)₂- structure | | wherein X in each case is halogen or CH₃ optionally halogenated;
or a pharmaceutically acceptable salt thereof.

2. A compound chosen from
N-(5-tert-Butyl-isoxazol-3-yl)-2-(4-methoxy-phenylamino)-2-methyl-propionamide
N-(5-tert-Butyl-isoxazol-3-yl)-2-isopropylamino-2-methyl-propionamide
2-sec-Butylamino-N-(5-tert-butyl-isoxazol-3-yl)-2-methyl-propionamide
N-(5-tert-Butyl-isoxazol-3-yl)-2-(isopropyl-methyl-amino)-2-methyl-propionamide
N-(5-tert-Butyl-isoxazol-3-yl)-2-morpholin-4-yl-isobutyramide
N-(5-tert-Butyl-isoxazol-3-yl)-2-cyclohexylamino-2-methyl-propionamide
2-Butylamino-N-(5-tert-butyl-isoxazol-3-yl)-2-methyl-propionamide
N-(5-tert-Butyl-isoxazol-3-yl)-2-(3-methyl-piperidin-1-yl)-isobutyramide
N-(5-tert-Butyl-isoxazol-3-yl)-2-(2-methyl-pyrrolidin-1-yl)-isobutyramide
N-(5-tert-Butyl-isoxazol-3-yl)-2-(4-methyl-piperidin-1-yl)-isobutyramide
N-(5-tert-Butyl-isoxazol-3-yl)-2-thiomorpholin-4-yl-isobutyramide
N-(5-tert-Butyl-isoxazol-3-yl)-2-cyclopropylamino-2-methyl-propionamide
N-(5-tert-Butyl-isoxazol-3-yl)-2-(2-methyl-piperidin-1-yl)-isobutyramide
N-(5-tert-Butyl-isoxazol-3-yl)-2-(4-methoxy-piperidin-1-yl)-isobutyramide
N-(5-tert-Butyl-isoxazol-3-yl)-2-piperidin-1-yl-isobutyramide
N-(5-tert-Butyl-isoxazol-3-yl)-2-pyrrolidin-1-yl-isobutyramide
N-(5-tert-Butyl-isoxazol-3-yl)-2-(4,4-difluoro-piperidin-1-yl)-isobutyramide
2-Cyclohexylamino-2-methyl-N-(5-trifluoromethyl-pyridin-2-yl)-propionamide
2-Piperidin-1-yl-N-(5-trifluoromethyl-pyridin-2-yl)-isobutyramide
N-(5-tert-Butyl-isoxazol-3-yl)-2-(5-chloro-indol-1-yl)-isobutyramide
2-(2-Aza-spiro[4.5]dec-2-yl)-N-(3-tert-butyl-isoxazol-5-yl)-isobutyramide
N-(3-tert-Butyl-isoxazol-5-yl)-2-methyl-2-[(tetrahydro-pyran-4-ylmethyl)-amino]-propionamide
N-(5-tert-Butyl-isoxazol-3-yl)-2-(4-chloro-phenoxy)-2-methyl-propionamide
N-(3-tert-Butyl-isoxazol-5-yl)-2-methyl-2-(tetrahydro-pyran-4-ylmethoxy)-propionamide
N-(5-tert-Butyl-isoxazol-3-yl)-2-methyl-2-[(tetrahydro-pyran-4-ylmethyl)-amino]-propionamide
N-(3-tert-Butyl-isoxazol-5-yl)-2-methyl-2-(tetrahydro-pyran-4-ylamino)-propionamide
N-(5-tert-Butyl-isoxazol-3-yl)-2-methyl-2-(tetrahydro-pyran-4-ylamino)-propionamide
2-Methyl-N-(5-phenyl-2H-1,2,4-triazol-3-yl)-2-[(tetrahydro-pyran-4-ylmethyl)-amino]-propionamide
2-Methyl-N-(5-phenyl-2H-1,2,4-triazol-3-yl)-2-(tetrahydro-pyran-4-ylamino)-propionamide
N-(3-tert-Butyl-isoxazol-5-yl)-2-methyl-2-(4-trifluoromethyl-phenylamino)-propionamide
N-(3-tert-Butyl-isoxazol-5-yl)-2-methyl-2-(5-trifluoromethyl-pyridin-2-ylamino)-propionamide
N-(5-tert-Butyl-isoxazol-3-yl)-2-methyl-2-(5-trifluoromethyl-pyridin-2-ylamino)-propionamide
N-(5-tert-Butyl-isoxazol-3-yl)-2-[(4-chloro-benzenesulfonyl)-methyl-amino]-2-methyl-propionamide
N-(5-tert-Butyl-isoxazol-3-yl)-2-[(4-fluoro-benzenesulfonyl)-methyl-amino]-2-methyl-propionamide
N-[1-(5-tert-Butyl-isoxazol-3-ylcarbamoyl)-1-methyl-ethyl]-4-chloro-N-methyl-benzamide
1,1-Dioxo-1λ6-thiomorpholine-4-carboxylic acid [1-(5-tert-butyl-isoxazol-3-ylcarbamoyl)-1-methyl-ethyl]-methyl-amide
N-(3-tert-Butyl-isoxazol-5-yl)-2-methyl-2-(tetrahydro-pyran-4-ylmethoxy)-propionamide
N-(5-tert-Butyl-isoxazol-3-yl)-2-methyl-2-(tetrahydro-pyran-4-ylmethoxy)-propionamide
N-(3-tert-Butyl-isoxazol-5-yl)-2-methyl-2-(tetrahydro-pyran-4-yloxy)-propionamide
N-(5-tert-Butyl-isoxazol-3-yl)-2-methyl-2-(tetrahydro-pyran-4-yloxy)-propionamide
2-Methyl-N-(5-phenyl-2H-1,2,4-triazol-3-yl)-2-(tetrahydro-pyran-4-ylmethoxy)-propionamide
2-Methyl-N-(5-phenyl-2H-1,2,4-triazol-3-yl)-2-(tetrahydro-pyran-4-yloxy)-propionamide and
N-(3-tert-Butyl-isoxazol-5-yl)-2-methyl-2-(5-trifluoromethyl-pyridin-2-yloxy)-propionamide
or a pharmaceutically acceptable salt thereof.

3. A pharmaceutical composition comprising a therapeutically effective amount of a compound according to claim 1 or 2.

4. A method of treating pain in an animal subject comprising administering to said animal subject a therapeutically effective dose of the compound according to claim 1 or 2.

5. The method according to claim 4 wherein pain is chosen from acute pain, visceral pain, neuropathic pain, inflammatory and nociceptive pain, cancer pain and headache.

* * * * *